(12) United States Patent
Barro Losada

(10) Patent No.: US 9,976,156 B2
(45) Date of Patent: May 22, 2018

(54) TRANSGENIC PLANTS

(71) Applicant: CONSEJO SUPERIOR DE INVESTIGACIONES CIENTIFICAS (CSIC), Madrid (ES)

(72) Inventor: Francisco Barro Losada, Cordova (ES)

(73) Assignee: Consejo Superior De Investigaciones Cientificas (CSIC), Madrid (ES)

( * ) Notice: Subject to any disclaimer, the term of this patent is extended or adjusted under 35 U.S.C. 154(b) by 107 days.

(21) Appl. No.: 14/899,698

(22) PCT Filed: Jun. 18, 2014

(86) PCT No.: PCT/EP2014/062870
§ 371 (c)(1),
(2) Date: Dec. 18, 2015

(87) PCT Pub. No.: WO2014/202688
PCT Pub. Date: Dec. 24, 2014

(65) Prior Publication Data
US 2016/0222400 A1    Aug. 4, 2016

(30) Foreign Application Priority Data
Jun. 18, 2013 (EP) ..................................... 13382228

(51) Int. Cl.
*C12N 15/82* (2006.01)
(52) U.S. Cl.
CPC ................ *C12N 15/8254* (2013.01)

(58) Field of Classification Search
CPC ............................ C12N 15/113; C12N 15/8254
See application file for complete search history.

(56) References Cited

U.S. PATENT DOCUMENTS 8,859,850 B2 * 10/2014 Losado .............. C12N 15/8218
435/320.1

FOREIGN PATENT DOCUMENTS

EP    2395089    12/2011

OTHER PUBLICATIONS

Gil-Humanes et al., J. Exp. Bot. (2011) 62 (12): 4203-4213.*
Ewart, J.A.D. (Mar. 1967) J. Sci. Fd Agric. vol. 18, pp. 111-116.*
Gil-Humanes, J. et al. J Exp Bot (2011) 62 (12): 4203-4213.*
Namath, Alexa, "GM Wheat Means Hope for Celiac Sufferers", Food Safety News, (Jan. 9, 2010), 2 pages. Jan. 9, 2010.
Gil-Humanes, Javier, et al, "Silencing of y-gliadins by RNA interference (RNAi) in bread wheat", Journal of Cereal Science, vol. 48, (Mar. 17, 2008), pp. 565-568. Mar. 17, 2008.
European Patent Office, "The International Search Report", issued in connection to International Application No. PCT/EP2014/062870, dated Sep. 18, 2014, 5 pages. dated Sep. 18, 2014.
Gil-Humanes, Javier, et al, "Suppression of Gliadins Results in Altered Protein Body Morphology in Wheat", Journal of Experimental Botany, vol. 62, No. 12, 11 Pgs. May 11, 2011.

* cited by examiner

*Primary Examiner* — Russell Kallis
(74) *Attorney, Agent, or Firm* — McKee, Voorhees & Sease, PLC

(57) ABSTRACT

The invention relates to methods for increasing total lysine content in plants and plant products and related uses.

19 Claims, 7 Drawing Sheets

A

B

C

A

B

C

TRANSGENIC PLANTS

FIELD OF THE INVENTION

Figure 1:
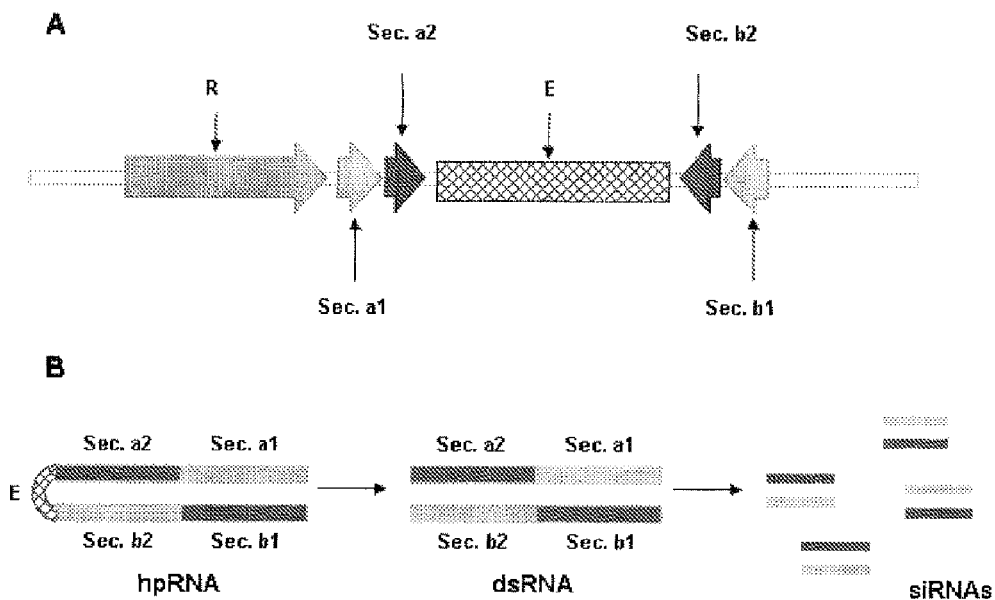

The invention relates to methods for producing transgenic plants with improved phenotypic traits and relates methods and uses.

INTRODUCTION

Humans and farm animals are unable to synthesize a number of essential amino acids, including lysine, and therefore need to obtain them from their diets. In developed countries, essential amino acids are generally provided from the dietary utilization of farm animals (particularly meat, eggs and milk) as well as from a variety of crop plants (particularly cereals and legumes) that together provide optimal levels of essential amino acids. In as far as crop plants are concerned, wheat is the dominant crop in temperate countries and is used for human food and livestock feed with over 600 million tonnes being harvested annually. However, lysine is a limiting amino acid in cereals, especially wheat. Cereal proteins have a low content of Lys (1.5-4.5 mol % vs. 5.5 mol % of WHO recommendation). It is estimated that the daily requirement for lysine in adults is 30 mg/kg per day and a diet limited in essential amino acids can lead to various signs of protein deficiencies in humans, such as lowered resistance to diseases, decreased blood proteins and retarded mental and physical development in young children. This is a particular problem in developing countries where the diet is mainly composed by a single cereal. Moreover, lysine is an important nutritional component in the feeds of livestock, which in turn contribute an extensive portion of the lysine required by humans (Galili et al, WHO Technical Report).

Therefore, enhancing the levels of lysine in the major crop plants is of nutritional importance. However, improving lysine content in plants has been difficult to achieve by classic breeding techniques. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. On the other hand, advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. Genetic engineering approaches have been successful in a limited number of crop plants, including soybean, rapeseed and maize. Mutant high-Lys lines have been obtained in maize opaque-2 mutants (Mertz et al) and opaque-2-derived QPM lines (Geevers et al, Glover et al); whereas genetic engineering approaches have been used to increase the lysine content in maize (Frizzi et al, Houmard et al) and rice (Wu et al).

It is therefore an object of the invention to address the shortcomings of the prior art and to provide a plant or plant products, in particular wheat and wheat products, with increased lysine content and thus increased nutritional value for humans and animals.

The inventors have demonstrated that plants with increased lysine content can be produced using RNA interference (RNAi) based on small interfering RNAs (siRNAs). The design of these siRNAs is disclosed in WO 2010/089437 incorporated herein by reference. As shown in WO 2010/089437, α (alpha), β (beta), γ (gamma), and ω (omega) gliadins of hard wheat and flour can be silenced by interference RNA (iRNA) through use of a polynucleotide that is transcribed into an hpRNA (hairpin RNA). By means of this polynucleotide, whose expression is specifically directed in particular to tissues of wheat seeds through gene expression-regulating sequences such as, for example, the promoter of a gene of γ gliadins or the promoter of the gene that codes for a D-hordein, one achieves post-transcriptional silencing of all of the genes of the species soft wheat and hard wheat in an effective and synergistic manner, as one is able to silence a greater number of gliadin genes compared to the results of silencing of α and γ gliadins by hpRNA described in the prior art. This is essentially due to the specific design of the sense and antisense subsequences whose generated siRNA hybridizes with all of the mRNA of the α, β, γ, and ω gliadins of wheat in combination with gliadin promoters having higher levels of expression that can be induced in specific tissues of the wheat seed.

RNAi is a technology based on the principle that small, specifically designed, chemically synthesized double-stranded RNA fragments can mediate specific messenger RNA (mRNA) degradation in the cytoplasm and hence selectively inhibit the synthesis of specific proteins. This technology has emerged as a very powerful tool to develop new compounds aimed at blocking and/or reducing anomalous activities in defined proteins. Compounds based on RNA interference can be rationally designed to block expression of any target gene, including genes for which traditional small molecule inhibitors cannot be found.

RNAi has been shown to occur in mammalian cells, not only through long double-stranded RNA (dsRNA) but by means of double-stranded siRNAs. siRNAs are molecules of double-stranded RNA of 21-25 nucleotides that originate from a longer precursor dsRNA.

According to current knowledge, the mechanism of RNAi is initiated when dsRNAs are processed by an RNase III-like protein known as Dicer. Precursor dsRNAs may be of endogenous origin, in which case they are referred to as miRNAs (encoded in the genome of the organism) or of exogenous origin (such as viruses or transgenes). The protein Dicer typically contains an N-terminal RNA helicase domain, an RNA-binding so-called Piwi/Argonaute/Zwille (PAZ) domain, two RNase III domains and a double-stranded RNA binding domain (dsRBD) and its activity leads to the processing of the long double stranded RNAs into 21-24 nucleotide double stranded siRNAs with 2 base 3' overhangs and a 5' phosphate and 3' hydroxyl group. Of the two strands of siRNA, only one, referred to as the guide strand, is incorporated into the enzymatic complex RISC (RNA-induced silencing complex), while the other strand is degraded. The thermodynamic characteristics of the 5' end of the siRNA determine which of the two strands is incorporated into the RISC complex. The strand that is less stable at the 5' end is normally incorporated as the guide strand, either because it has a higher content of AU bases or because of imperfect pairings. The guide strand must be complementary to the mRNA to be silenced in order for post-transcriptional silencing to occur.

The resulting siRNA duplexes are then incorporated into the effector complex RISC, where the antisense or guide strand of the siRNA guides RISC to recognize and cleave target mRNA sequences upon adenosine-triphosphate (ATP)-dependent unwinding of the double-stranded siRNA molecule through an RNA helicase activity. The catalytic activity of RISC, which leads to mRNA degradation, is mediated by the endonuclease Argonaute 2 (AGO2). AGO2 belongs to the highly conserved Argonaute family of proteins. Argonaute proteins are ~100 KDa highly basic proteins that contain two common domains, namely PIWI and PAZ domains. The PIWI domain is crucial for the interaction with Dicer and contains the nuclease activity responsible for the cleavage of mRNAs. AGO2 uses one strand of the siRNA duplex as a guide to find messenger RNAs containing complementary sequences and cleaves the phosphodiester backbone between bases 10 and 11 relative to the guide strand's 5' end. An important step during the activation of RISC is the cleavage of the sense or passenger strand by AGO2, removing this strand from the complex. Crystallography studies analyzing the interaction between the siRNA guide strand and the PIWI domain reveal that it is only nucleotides 2 to 8 that constitute a "seed sequence" that directs target mRNA recognition by RISC, and that a mismatch of a single nucleotide in this sequence may drastically affect silencing capability of the molecule. Once the mRNA has been cleaved, and due to the presence of unprotected RNA ends in the fragments, the mRNA is further cleaved and degraded by intracellular nucleases and will no longer be translated into proteins while RISC will be recycled for subsequent rounds. This constitutes a catalytic process leading to the selective reduction of specific mRNA molecules and the corresponding proteins. It is possible to exploit this native mechanism for gene silencing with the purpose of regulating any gene(s) of choice by directly delivering siRNA effectors into the cells or tissues, where they will activate RISC and produce a potent and specific silencing of the targeted mRNA.

SUMMARY OF THE INVENTION

In a first aspect, the invention relates to a method for increasing lysine content in a plant, plant part or plant product derived therefrom comprising introducing and expressing a polynucleotide that is at least 80%, at least 90% or at least 95% identical to a sequence comprising two sequence pairs (a1-a2) and (b2-b1) separated by a spacer sequence in which:
 a. the sequences a1, a2, b1, and b2 are different sequences and are selected from SEQ ID NO: 1, SEQ ID NO: 2, SEQ ID NO: 3, or SEQ ID NO: 4, wherein
 b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
 c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4.

In a second aspect, the invention relates to a method for increasing lysine content in a food or feed composition comprising
 a) introducing and expressing a nucleic acid construct comprising a polynucleotide that is at least 80%, at least 90% or at least 95% identical to a sequence comprising two sequence pairs (a1-a2) and (b2-b1) separated by a spacer sequence in which:
  a. the sequences a1, a2, b1, and b2 are different sequences and are selected from SEQ ID NO: 1, SEQ ID NO: 2, SEQ ID NO: 3, or SEQ ID NO: 4, wherein
  b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
  c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4 in a plant
 b) obtaining a progeny plant derived from the plant of step a) and
 c) preparing a food composition from said plant or part thereof.

In another aspect, the invention relates to a use of a nucleic acid construct comprising a polynucleotide that is at least 80%, at least 90% or at least 95% identical to a sequence comprising two sequence pairs (a1-a2) and (b2-b1) separated by a spacer sequence in which:
 a. the sequences a1, a2, b1, and b2 are different sequences and are selected from SEQ ID NO: 1, SEQ ID NO: 2, SEQ ID NO: 3, or SEQ ID NO:4, wherein
 b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
 c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4
in increasing lysine content in a plant, plant part thereof or plant product.

In another aspect, the invention relates to a method for providing improved nutrition to a human or animal comprising feeding said human or animal on a diet comprising a food composition obtained by producing a plant or plant product with increased lysine content said method comprising
 a) introducing into said plant and expressing a polynucleotide that is at least 80%, at least 90% or at least 95% identical to a sequence comprising two sequence pairs (a1-a2) and (b2-b1) separated by a spacer sequence in which:
  a. the sequences a1, a2, b1, and b2 are different sequences and are selected from SEQ ID NO: 1, SEQ ID NO: 2, SEQ ID NO: 3, or SEQ ID NO: 4, wherein
  b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
  c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4
 b) obtaining a progeny plant derived from said plant and
 c) and preparing a food composition from said plant or plant part.

In another aspect, the invention relates to a method for treating a condition associated with lysine deficiency comprising providing in the diet of a person or administering to a person or patient in need thereof an efficient amount of a food composition or food supplement obtained by producing a plant or plant product with increased lysine content said method comprising
 a) introducing into said plant and expressing a polynucleotide that is at least 80%, at least 90% or at least 95% identical to a sequence comprising two sequence pairs (a1-a2) and (b2-b1) separated by a spacer sequence in which:
  a. the sequences a1, a2, b1, and b2 are different sequences and are selected from SEQ ID NO: 1, SEQ ID NO: 2, SEQ ID NO: 3, or SEQ ID NO: 4, wherein
  b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4
   b) obtaining a progeny plant derived from said plant and
   c) preparing a food composition or food supplement from said plant or plant part.

Any of the methods described above may comprise the additional step of choosing a regenerated plant with an increased lysine content. The methods may comprise the additional steps of screening plants for those that comprise the polynucleotide construct above and which have an increased lysine content and selecting a plant that has an increased lysine content. In another embodiment, steps or further steps include measuring the lysine content in said plant progeny, part thereof or product derived there from and optionally comparing the lysine content to that of a control plant, preferably a wild type plant. Harvesting lysine rich plant material, such as seeds, may also be included. In a preferred embodiment, the plant is wheat.

FIGURES

FIG. 1. Shows the structure of the polynucleotide

Figure A shows a polynucleotide that comprises the sequence pairs a1-a2 and b2-b1, separated by a spacer sequence (E) whose expression is directed by a gene expression-regulating sequence (R).

Figure B shows the hpRNA resulting from transcription of the polynucleotide represented in Figure A in which is formed a hairpin, in which the sequences Sec a1, a2, b2, and b1 hybridize as is described. Subsequently, this RNA is processed, producing a new sequence of double-stranded RNA (dsRNA). The final step shown refers to cleaving the sequence by enzymes such as, for example, the enzyme Dicer, such that double-stranded RNA sequences of approximately 21-25 nucleotides, referred to as siRNA (small interfering RNA), are formed.

Figure 2:
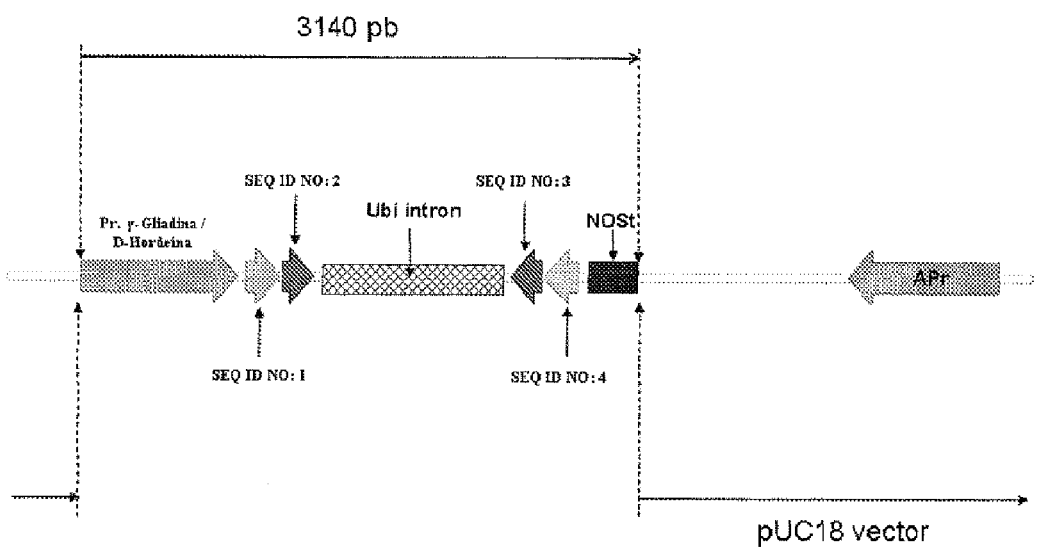

FIG. 2. An example of the polynucleotide.

In this case, the sequence R is a promoter sequence of the gene of gamma-gliadin (γ gliadin) or D-hordein gene. Sequence E is a fragment of an intron of the maize ubiquitin gene. NOSt is a transcription termination sequence. This polynucleotide is inserted in this specific example into a pUC18 vector that has an ampicillin resistance gene.

Figure 3:
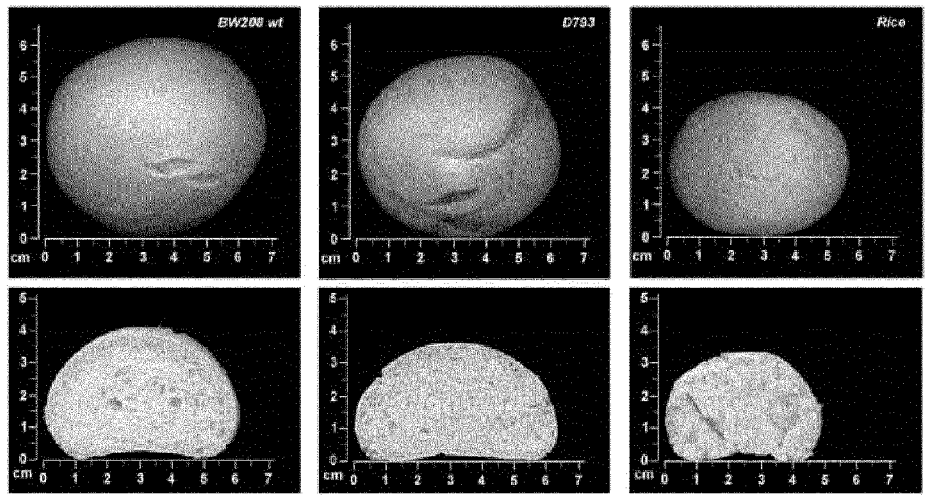
Figure 3:
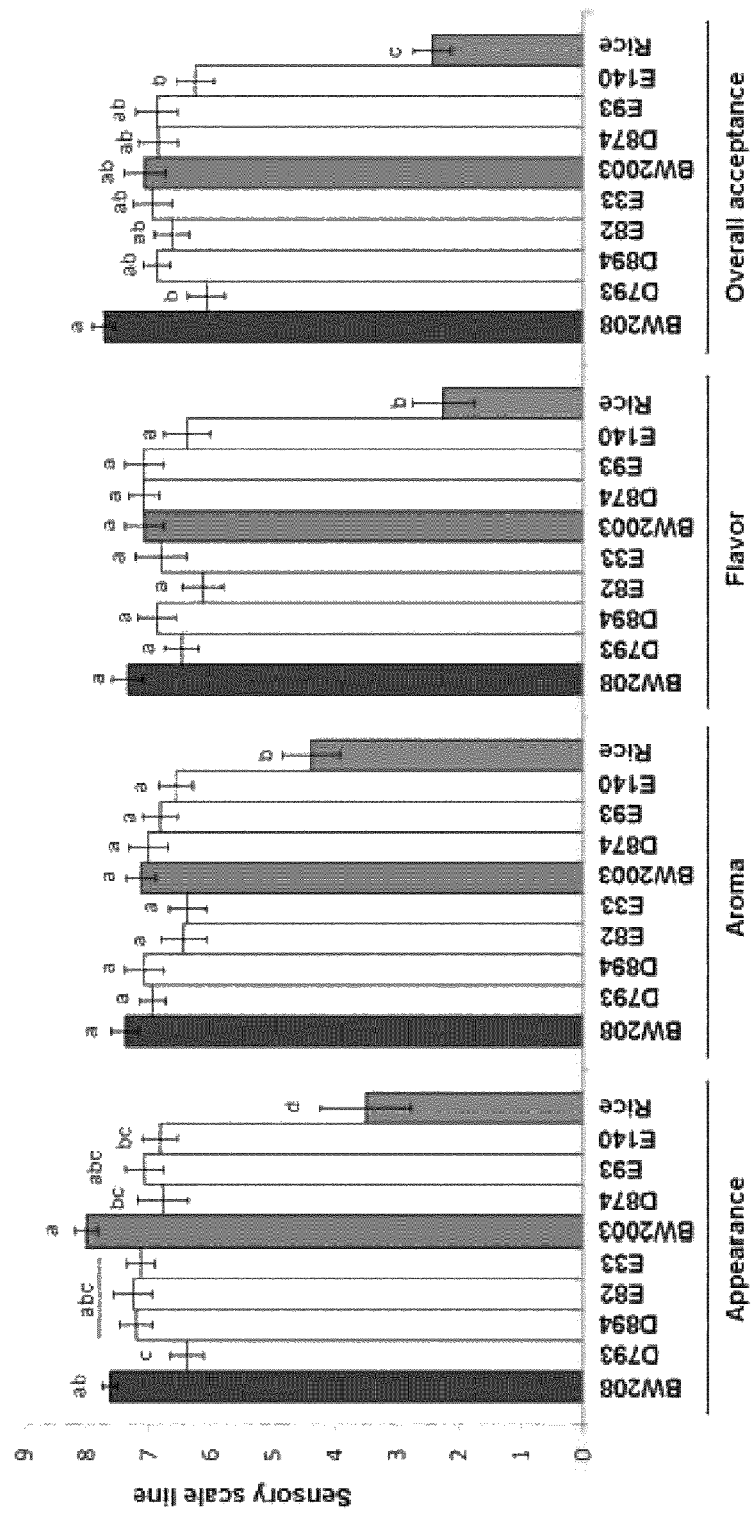
Figure 3:
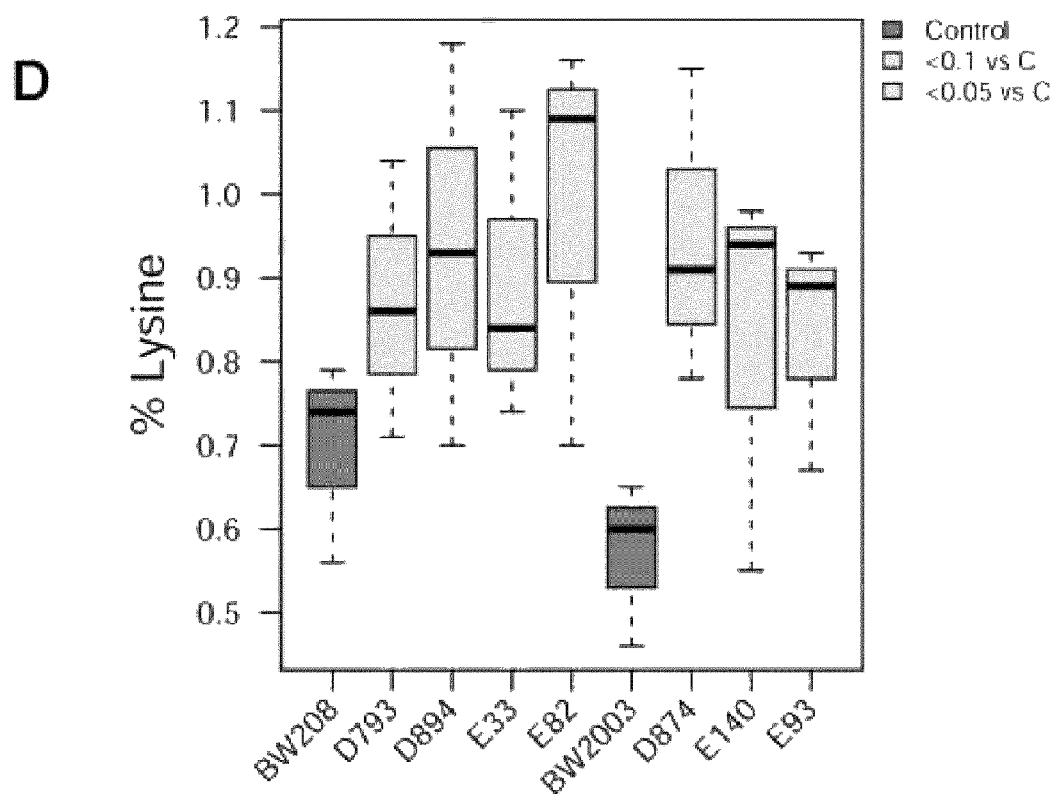

FIG. 3. Bread made from flour of transgenic plants and lysine content. Physical and organoleptic properties, and increased content of lysine. (A) Loaves and slices of wild-type BW208, transgenic line D793, and rice (as a control). (B) Physical properties of bread loaves obtained from wild-type lines, transgenic lines, and rice. (C) Descriptive sensory analysis. Lines with the same letter indicate that no significant differences exist among them as determined by the Tukey HSD post hoc all-pairwise comparison test (P<0.05). Sensory scale ranges from 1-9. In addition, most of the transgenic lines showed statistically comparable levels of quality in comparison with their wild type counterparts. The overall acceptance had an average score of 7.4 for the wild types and 6.6 for the transgenic lines (with no significant differences found between most lines and wild types). In contrast, the overall acceptance of the rice was significantly lower, presenting a score of 2.4. This indicates that there are no differences in terms of quality between transgenic breads and normal wheat flour. (D) Box-and-whisker plot of lysine content (%) in flour from wild types and transgenic lines. Dark grey boxes represent the wild-type lines. Significant differences between transgenic lines and their respective controls are indicated in pale grey (P<0.1), and pale orange (P<0.05).

Figure 4:
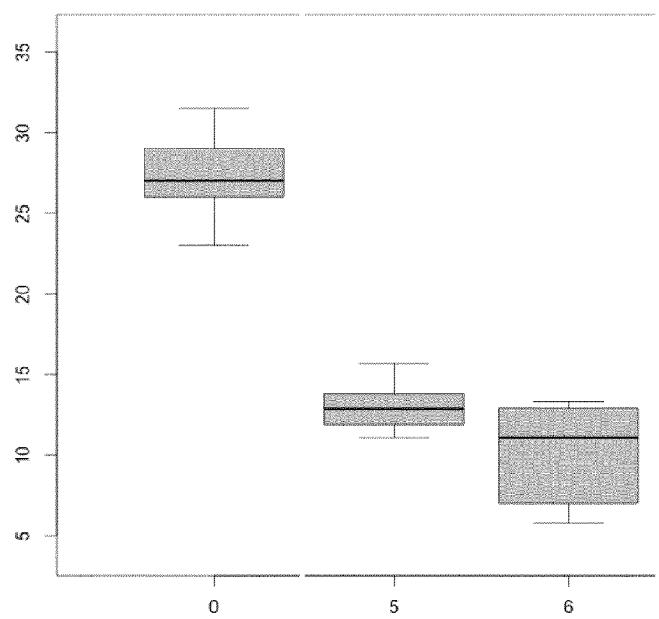
Figure 4:
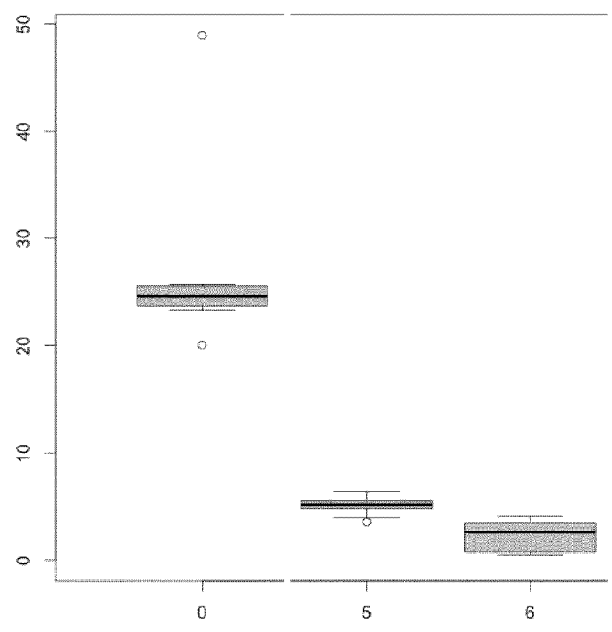
Figure 4:
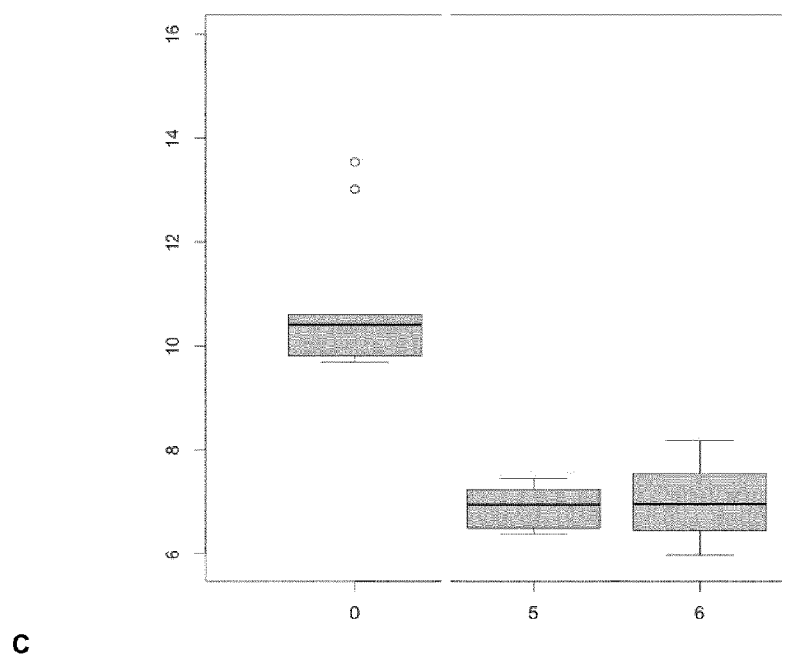

FIG. 4 Comparative gliadin content for plasmid combinations 5 and 6 with respect to the wild type
   (A) Alpha gliadins μg/mg flour
   (B) Gamma gliadins μg/mg flour
   (C) Omega gliadins μg/mg flour

| RNAi Combinations | Plasmid |
|---|---|
| 0 | Na, wild type |
| 5 | pDhp_ω/α |
| 6 | pGhp_ω/α |

Figure 5:
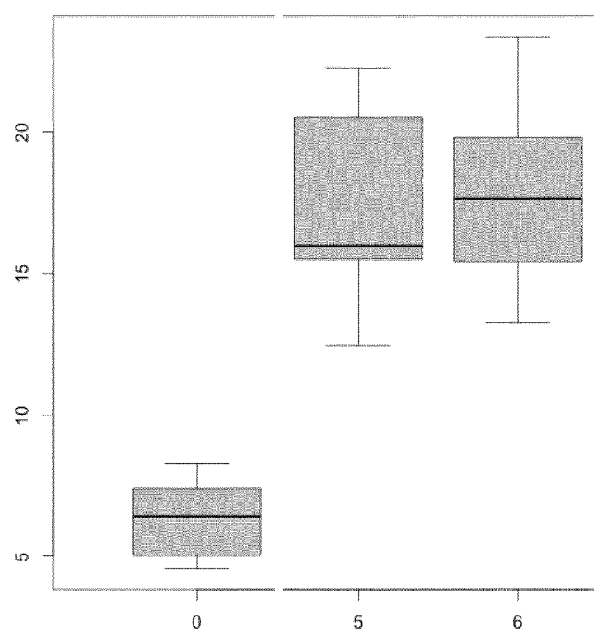
Figure 5:
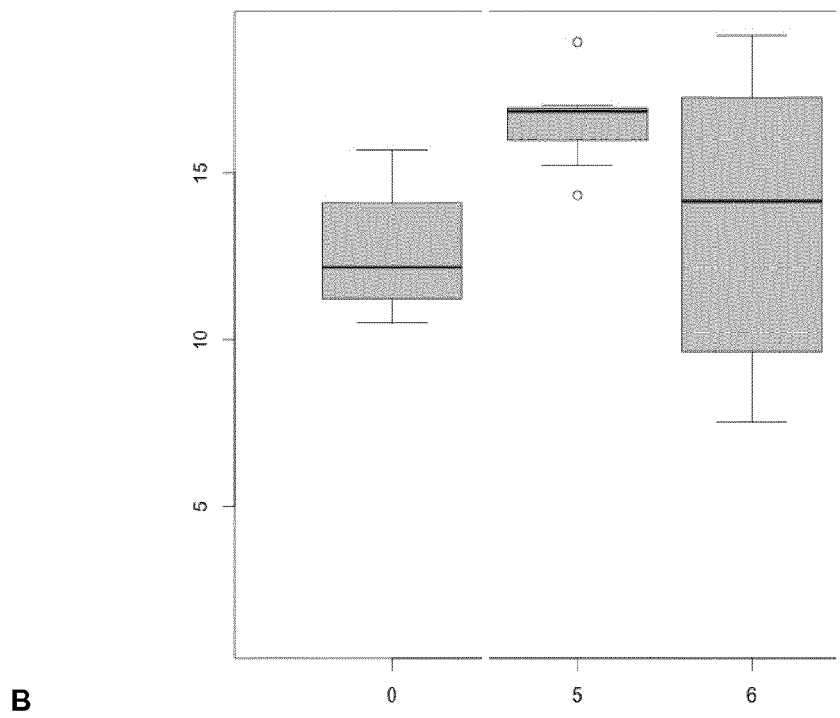
Figure 5:
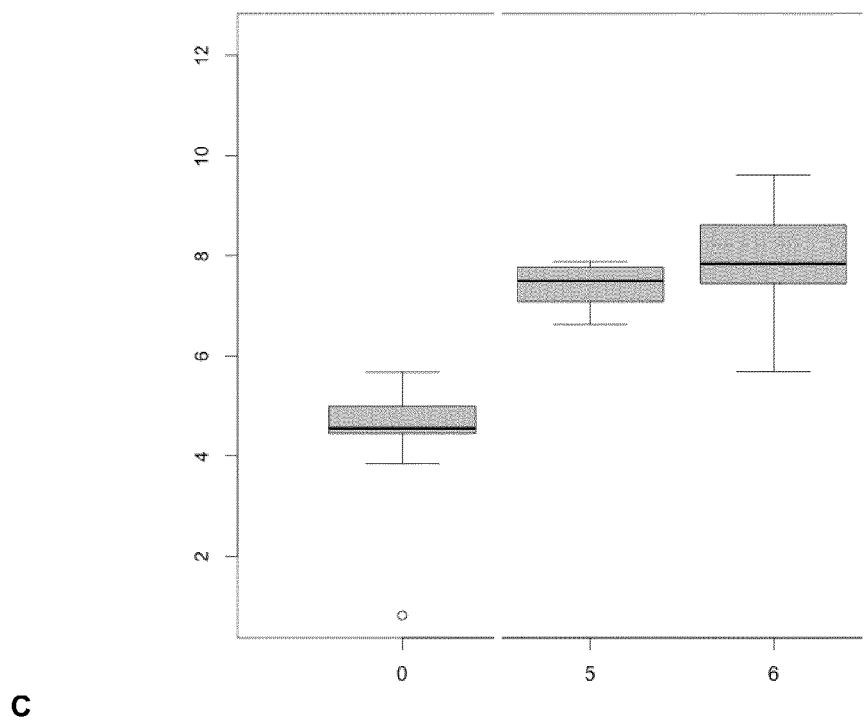

FIG. 5 Comparative glutenin content
   (A) and (B) Comparative glutenin content for plasmid combinations 5 and 6 with respect to the wild type
   (A) HMW μg/mg flour
   (B) LMW μg/mg flour
   (C) Comparative non-gluten protein content for plasmid combinations 5 and 6 with respect to the wild type in μg/mg flour.

| RNAi Combinations | Plasmid |
|---|---|
| 0 | Na, wild type |
| 5 | pDhp_ω/α |
| 6 | PGhp_ω/α |

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA, siRNA, sRNA, dsRNA, miRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs, CDS or genomic DNA in combination with regulatory sequences.

The terms "peptide", "polypeptide" and "protein" are used interchangeably herein and refer to amino acids in a polymeric form of any length, linked together by peptide bonds.

For the purposes of the invention, "transgenic", "transgene" or "recombinant" means with regard to, for example, a nucleic acid sequence, specifically an RNA nucleic acid sequence or molecule, an expression cassette, gene construct, or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815 both incorporated by reference.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. For the purposes of the invention, "transgenic", preferably means that the nucleic acids is expressed homologously. However, as mentioned, transgenic also means that, while the nucleic acids according to the different embodiments of the invention are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. According to the invention, the transgene is integrated into the plant in a stable manner and the plant is preferably homozygous for the transgene. As used herein, a "stably" transformed plant is a plant in which the exogenous DNA or RNA is heritable. The exogenous DNA or RNA may be heritable as a fragment of DNA maintained in the plant cell and not inserted into the host genome. Preferably, the stably transformed plant comprises the exogenous DNA or RNA. As used herein "progeny" means any subsequent generation, including the seeds and plants therefrom, which is derived from a particular parental plant or set of parental plants; the resultant progeny may be substantially homozygous or substantially homozygous, depending upon pedigree. Progeny of a transgenic plant of this present invention can be, for example, self-pollinated, crossed to another transgenic plant, crossed to a non-transgenic plant, and/or back crossed to an ancestor.

As used herein "siNAs" of the invention refers to a double stranded oligonucleotide capable of mediating target mRNA cleavage via RNA interference.

The aspects of the invention involve recombination DNA technology and in a preferred embodiment exclude embodiments that are solely based on generating plants by traditional breeding methods.

In a first aspect, the invention relates to a method for increasing lysine content in a plant, part thereof or plant product comprising a) introducing and expressing a polynucleotide that is at least 80%, at least 90% or at least 95% identical to a sequence comprising two sequence pairs (a1-a2) and (b2-b1) separated by a spacer sequence in which:

a. the sequences a1, a2, b1, and b2 are different sequences and are selected from SEQ ID NO: 1, SEQ ID NO: 2, SEQ ID NO: 3, or SEQ ID NO: 4 wherein b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4.

In another aspect, the invention relates to the use of a polynucleotide that is at least 80%, at least 90% or at least 95% identical to a sequence comprising two sequence pairs (a1-a2) and (b2-b1) separated by a spacer sequence in which:

a. the sequences a1, a2, b1, and b2 are different sequences and are selected from SEQ ID NO: 1, SEQ ID NO: 2, SEQ ID NO: 3, or SEQ ID NO: 4, wherein b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4 in increasing lysine content in a plant, plant product.

The use may include the step of transforming a plant with said polypeptide.

A plant product according to the invention can be a food or feed composition obtained from the plant or part thereof expressing a polynucleotide as described herein. A food composition is for human consumption, is made using preferably plant seeds and is selected from, but not limited to, bread or other bakery products comprising flour, pasta, dumplings or cereal based drinks. The term food composition also includes vitamin supplements and nutritional supplements.

A feed composition is a feed composition for animal consumption that is made using plants of parts thereof, preferably harvestable parts such as plant seeds.

Thus, in one embodiment, the invention therefore relates to a method for increasing lysine content in a food or feed composition comprising a) introducing and expressing a polynucleotide that is at least 80%, at least 90%, at least 95% identical to a sequence comprising two sequence pairs (a1-a2) and (b2-b1) separated by a spacer sequence in which:

a. the sequences a1, a2, b1, and b2 are different sequences and are selected from SEQ ID NO: 1, SEQ ID NO: 2, SEQ ID NO: 3, or SEQ ID NO: 4 wherein
b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4.

In one embodiment, the composition is a feed composition. In one embodiment, the composition is a food composition. The method may further comprise the step of choosing a regenerated plant with increased lysine content. Optional additional steps are set out below.

The method may further comprise the steps of
b) selecting a lysine enriched part of said plant;
c) harvesting parts of a plant enriched in lysine and
d) obtaining a feed composition.

According to the various aspects of the invention, lysine content is increased compared to a control plant, plant part thereof or control plant product. The control plant does not express the polynucleotide as described herein.

A control plant as used herein is a plant, which has not been modified according to the methods of the invention. Accordingly, the control plant has not been genetically modified to express a nucleic acid as described herein. In one embodiment, the control plant is preferably a wild type (WT) plant. For example, if the plant is wheat, then in one embodiment, then control plant is wild type wheat. In another embodiment, the control plant is a plant that does not carry a transgene according to the methods described herein, but expresses a different transgene. The control plant is typically of the same plant species, preferably the same variety or ecotype as the plant to be assessed.

A control plant or plant cell may thus comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest or (e) the subject plant or plant cell itself, under conditions in which the gene of interest is not expressed.

In one embodiment, the method for increasing lysine content in a plant, part thereof or plant product described above further comprises the step of choosing a regenerated plant with increased lysine content. It may also comprise the additional steps of obtaining a progeny plant, that is a regenerated plant, derived from said plant and selecting a lysine enriched part of said plant. Selecting a lysine enriched part can be carried out by assessing lysine content in said plant and comparing lysine content to a wild type plant. The lysine enriched part is, in one embodiment, seeds. The method may also comprise the step of harvesting the lysine rich part.

The method may also optionally comprise the steps of screening plants for those that comprise the polynucleotide construct above and which have an increased lysine content and selecting or choosing a plant that has an increased lysine content. In another embodiment, further steps include measuring the lysine content in said plant progeny, part thereof or product derived therefrom and comparing the lysine content to that of a control plant.

Preferably, according to the methods described herein, the progeny plant is stably transformed and comprises the exogenous polynucleotide which is heritable as a fragment of DNA maintained in the plant cell and the method may include steps to verify that the construct is stably integrated. The method may also comprise the additional step of collecting seeds from the selected progeny plant and producing a food or feed composition.

Thus, in one embodiment, the invention relates to a method for increasing lysine content in a plant, plant part or plant product derived therefrom comprising a) introducing and expressing a polynucleotide that is at least 80%, at least 90%, at least 95% identical to a sequence comprising two sequence pairs (a1-a2) and (b2-b1) separated by a spacer sequence in which:
a. the sequences a1, a2, b1, and b2 are different sequences and are selected from SEQ ID NO: 1, SEQ ID NO: 2, SEQ ID NO: 3, or SEQ ID NO: 4, wherein
b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4;
b) obtaining a progeny plant derived from said plant and
c) selecting or choosing a lysine enriched plant or part of said plant.

Selecting a lysine enriched part can be carried out by comparing lysine content to a wild type plant. The lysine enriched part is, in one embodiment, seeds. The method may also comprise the step of harvesting the lysine rich part.

The method may also optionally comprise the steps of screening plants for those that comprise the polynucleotide construct above and which have increased lysine content and selecting a plant that has an increased lysine content. In another embodiment, further steps include measuring the lysine content in said plant progeny, part thereof or product derived therefrom and comparing the lysine content to that of a control plant. The method may also comprise the additional step of producing a food or feed composition.

In another embodiment, the invention relates to a method for increasing lysine content in a plant, plant part or plant product derived therefrom comprising a) introducing and expressing a polynucleotide that is at least 80%, at least 90%, at least 95% identical to a sequence comprising two sequence pairs (a1-a2) and (b2-b1) separated by a spacer sequence in which:
a. the sequences a1, a2, b1, and b2 are different sequences and are selected from SEQ ID NO: 1, SEQ ID NO: 2, SEQ ID NO: 3, or SEQ ID NO: 4, wherein
b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4;
b) obtaining a progeny plant derived from said plant;
c) measuring the lysine content in said plant progeny, plant part or plant product derived therefrom and
d) comparing the lysine content to that of a control plant.

The method may also comprise the additional step of producing a food or feed composition. This is rich in lysine compared to a control plant or part thereof or food or feed composition.

In one embodiment of the various aspects of the invention, lysine content is increased in plant seeds or grain, for example wheat grain. As shown in the examples, products derived from a plant expressing a polynucleotide as above can be processed in the same way as control plants. A transgenic seed of the present invention with increased lysine is especially useful as a feed or food product, a source of purified plant protein products, or a source of other products processed from the seed that contain a higher lysine content than a control plant or part thereof of a similar variety. In certain embodiments, seed obtained have a sufficient quantity of lysine such that the livestock feed or food product made from the grain does not require supplementation from additional lysine sources. The high lysine seed described herein achieves this level of lysine production and accumulation.

As also shown in the examples, non-gluten proteins rich in lysine are upregulated in the transgenic plants. Therefore, the methods described herein can also be used to upregulate non-gluten proteins compared to a control plant.

For example, the invention also relates to a method for upregulate non-gluten protein content in a plant, plant part or plant product derived therefrom comprising introducing and expressing a polynucleotide that is at least 80%, at least 90% or at least 95% identical to a sequence comprising two sequence pairs (a1-a2) and (b2-b1) separated by a spacer sequence in which:
   a. the sequences a1, a2, b1, and b2 are different sequences and are selected from SEQ ID NO: 1, SEQ ID NO: 2, SEQ ID NO: 3, or SEQ ID NO: 4, wherein
   b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
   c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4.

The term lysine content refers to total lysine content. According to the various aspects of the invention, lysine content can be measured using standard methods described in the art and as shown in the examples. It can be measured as part of the total amino acid content in proteins and/or as the free amino acid content following protein hydrolysis. In one embodiment, it is measured following protein hydrolysis and lysine that forms part of proteins as well as free lysine is thus measured.

Preferably, the lysine content is measured in a plant product, for example flour, such as wholemeal flour, obtained from grain of transgenic plants expressing the polynucleotide according to the methods described herein.

These methods may require preliminary treatment of the test material to hydrolyse the proteins to the free amino acids as described in the art. The amino acids are the analysed using chromatographic separation of the amino acids present in the test sample using by column technique. Within the various techniques using columns for separation, a major subdivision can be made into pre- and post-column derivatization procedures. Ion-exchange chromatography uses post-column derivatization in that the amino acids are separated by means of ion exchange, and derivatives are formed after they have emerged from the column so that they may be quantified. The most common derivatization procedure is that using ninhydrin with subsequent determination of optical density. In contrast, pre-column derivatization, as is used for gas-liquid chromatography (GLC) and high-performance liquid chromatography (HPLC), uses columns to separate the amino acid derivatives. These derivatives, after emerging from the column, are then quantified by various detection devices.

In High-Performance Liquid Chromatography (HPLC), pre-column derivatization is required for amino acid analysis. Dansyl chloride (5-dimethylamino-1-naphthalene sulphonyl chloride) is frequently used for this purpose, producing fluorescent dansyl derivatives that are separated by a reversed phase column chromatographic procedure. The column employs silica gel with attached non-polar hydrocarbon functional groups (e.g., octadecyl moieties) as the stationary phase and uses a multi-step non-linear elusion procedure. Among other eluents, acetonitrile and water mixtures have been suggested for the separation of dansylated amino acids. These are then detected and measured by a fluorescence detector, which can provide detection limits in the picogram range. Alternatively, Ion-Exchange Chromatography Ion-exchange chromatography can be used in amino acid analysis. In this method, lithium or sodium buffers, narrow columns with fine spherical resin particles, and fluorescamine or ninhydrin, are used. Other methods include is Gas-Liquid Chromatography which requires the quantitative conversion of the amino acids to volatile derivatives or Thin-Layer Chromatography (TLC).

Preferably, according to the various aspects of the invention, lysine content in the plant or part thereof, for example in the seed, or in a plant product, for example flour or bread, is increased or enhanced by about 10% to about 80% compared to the control (preferably wild type), preferably about 20% to about 70%, for example 20%, 25%, 30%, 35% 40% or 45%, more preferably about 24% to about 67%

For example, as shown in table 4, the lysine content in flour obtained from a wild type plant is about 0.57% to about 0.70% (% w/w), depending on the cultivar used. The lysine content in flour obtained from a transgenic plant is more than about 0.7%, for example more than about 0.7% to about 0.98%, for example 0.7%, 0.75%, 0.8%, 0.85%, 0.9%, 0.95% (% w/w).

A lysine rich plant or part thereof as described herein has increased lysine content as defined above.

The sequences a1-a2 and b2-b1 in the polypeptide used in the various aspects of the invention described herein are linked to form a linear and continuous nucleotide sequence in which the two pairs are linked by a spacer sequence. Preferably, the spacer sequence is a non-coding sequence that is eliminated after the process of forming dsRNA. The spacer sequence may be part of a sequence of an intron of a gene. The function of the spacer sequence is to act as a hinge for the sequence pairs described so that pairing or hybridization of the RNA sequences coding for the polynucleotide may take place.

The polynucleotide used in the various aspects of the invention described herein is a polynucleotide that comprises two sequence pairs (a1-a2) and (b2-b1) separated by a spacer sequence in which the sequences a1, a2, b1, and b2 are described above. The sequences a1-a2 and b2-b1 (referred to in the following as the sequence pairs of the invention) are linked to form a linear and continuous nucleotide sequence in which, in turn, the two pairs are linked by means of a spacer sequence at least one nucleotide in length.

The polynucleotide comprises sequences a1-a2 and b2-b1 which are selected from SEQ ID NO: 1, 2, 3 and 4 as shown in tables 1 and 2 is at least 80%, preferably at least 90%, preferably at least 95% identical with the polynucleotide comprising sequences a1-a2 and b2-b1 selected from SEQ ID NO: 1, 2, 3 and 4 as shown in Tables 1 and 2. Sequence identity is, for example, at least 81%, 82%, 83%, 84%, 85%, 86%, 87%, 88%, 89%, 90%, 91%, 92%, 93%, 94%, 95%, 96%, 97%, 98% or 99%. In one embodiment, sequence identity is 100%. The polynucleotide comprises sequences a1, a2, b1, and b2 which are all different sequences, that is they all differ from each other, and are selected from SEQ ID NO: 1, SEQ ID NO: 2, SEQ ID NO: 3, or SEQ ID NO: 4 respectively or sequences with at least 90% homology to one or more of these sequences. In one embodiment, sequence identity is at least 90%, 91%, 92%, 93%, 94%, 95%, 96%, 97%, 98% or 99%. Thus, in one embodiment a1 consists of or comprises SEQ ID NO:1 or a sequence with at least 90%, 91%, 92%, 93%, 94%, 95%, 96%, 97%, 98% or 99% sequence identity thereto, a2 consists of or comprises SEQ ID NO:2 or a sequence with at least 90%, 91%, 92%, 93%, 94%, 95%, 96%, 97%, 98% or 99% sequence identity thereto, b1 consists of or comprises SEQ ID NO:3 or a sequence with at least 90%, 91%, 92%, 93%, 94%, 95%, 96%, 97%, 98% or 99% sequence identity thereto and b2 consists of or comprises SEQ ID NO:4 or a sequence with at least 90%, 91%, 92%, 93%, 94%, 95%, 96%, 97%, 98% or 99% sequence identity thereto.

In one embodiment, sequences a1, a2, b1, and b2 are all different sequences and are selected from SEQ ID NO: 1, SEQ ID NO: 2, SEQ ID NO: 3 or SEQ ID NO: 4. Thus, in one embodiment a1 consists of or comprises SEQ ID NO: 1, a2 consists of or comprises SEQ ID NO:2, b1 consists of or comprises SEQ ID NO:3 and b2 consists of or comprises SEQ ID NO:4.

SEQ ID NO: 1 is a sense sequence that comprises a part of the fragment that codes for the epitopes of ω gliadins recognized by human T cells that give rise to an immune response in persons suffering from celiac disease. SEQ ID NO: 2 is the sense sequence that comprises a part of the fragment that codes for the epitopes of α, β, and γ gliadins. SEQ ID NO: 3 is the antisense sequence of SEQ ID NO: 2, and SEQ ID NO: 4 is the antisense sequence of SEQ ID NO: 1.

The polynucleotide used in the various aspects of the invention gives rise to RNA in which the two sequence pairs hybridize thus forming a hairpin. The polynucleotide used according to the various aspects of the invention covers various combinations of sequences through which RNA hairpins can be obtained are shown in Table 1 and Table 2. Any of these combinations can be used according to the various embodiments of the invention. The RNA sequence coded for by the polynucleotide described herein is capable of forming an hpRNA in which the sequence coded for by the pair a1-a2 completely hybridizes with the sequence coded for by the pair b2-b1. An hpRNA is a hairpin shape formed by hybridization of the transcribed sequences. In the present invention, the polynucleotide in the various aspects was used as a template for synthesizing the transcribed sequences, as can be seen in FIG. 1B. An hpRNA is a double-stranded RNA (dsRNA) that is cleaved by an endoribonuclease, for example the endoribonuclease Dicer, resulting in fragments of approximately 21-25 nts. These fragments are known as siRNA. As has been described above, the siRNAs cause post-transcriptional silencing of the target nucleotide sequences so that no protein is obtained.

In another embodiment, the polynucleotide according the aspects of the invention, is at least one siRNA generated from the sequence of the hpRNA according to the previous aspect. The siRNA can also be referred to as RNAi. The siRNA is a double-stranded RNA of between 21 and 25 nucleotides, but is not limited to this number of nucleotides, and it is generated from the hpRNA sequence of the invention. In the present invention, in defining the approximate number of nucleotides of the siRNA (approximately 21 and 25 nucleotides), it is understood that there is another strand that is complementary to this sequence, i.e., that one can use the terms nucleotides or base pairs (bp) interchangeably.

As has been described, the Dicer enzyme cleaves the dsRNA into double-stranded fragments of approximately 21-25 nucleotides (siRNA), with the 5' end phosphorylated and two unpaired nucleotides protruding at the 3' end. Of the two strands of siRNA, only one, referred to as the guide strand, is incorporated into the enzymatic complex RISC, while the other is degraded. The thermodynamic characteristics of the 5' end of the siRNA determine which of the two strands is incorporated into the RISC complex. The strand that is less stable at the 5' end is normally incorporated as the guide strand. The guide strand must be complementary to the mRNA that is to be silenced in order for post-transcriptional silencing to occur. Subsequently, the RISC complex binds to the complementary mRNA of the guide strand of the siRNA present in the complex, and cleavage of the mRNA occurs.

In another aspect, the polynucleotide may be an RNA sequence coded for by any of the polynucleotides above and capable of forming an hpRNA in which the sequence coded for by the pair a1-a2 hybridizes completely with the sequence coded for by the pair b2-b1. In another aspect, the polynucleotide may be an siRNA generated from the sequence of the hpRNA.

Table 1. Combinations of sequences for the polynucleotide according to the aspects of the invention in which the a1-a2 and b2-b1 pairs are sense or antisense sequences. The sequences may be selected from SEQ ID NO: 1, SEQ ID NO: 2, SEQ ID NO: 3, or SEQ ID NO: 4. In another embodiment, the sequences may be selected from sequences with at least 80%, 90% or at least 95% homology to SEQ ID NO: 1, SEQ ID NO: 2, SEQ ID NO: 3, and/or SEQ ID NO: 4

| Combinations | a1 | a2 | b2 | b1 |
|---|---|---|---|---|
| 1 | SEQ ID NO: 1 | SEQ ID NO: 2 | SEQ ID NO: 3 | SEQ ID NO: 4 |
| 2 | SEQ ID NO: 2 | SEQ ID NO: 1 | SEQ ID NO: 4 | SEQ ID NO: 3 |
| 3 | SEQ ID NO: 3 | SEQ ID NO: 4 | SEQ ID NO: 1 | SEQ ID NO: 2 |
| 4 | SEQ ID NO: 4 | SEQ ID NO: 3 | SEQ ID NO: 2 | SEQ ID NO: 1 |

In one embodiment, the combination of sequence pairs is combination 1 as shown above. In one embodiment, the combination of sequence pairs is combination 2 as shown above. In one embodiment, the combination of sequence pairs is combination 3 as shown above. In one embodiment according to the various aspects of the invention, the combination of sequence pairs is combination 4 as shown above.

Table 2. Combinations of sequences for the polynucleotide according to the aspects of the invention in which the a1-a2 and b2-b1 pairs contain sense and antisense sequences. The sequences may be selected from SEQ ID NO: 1, SEQ ID NO: 2, SEQ ID NO: 3, or SEQ ID NO: 4. In another embodiment, the sequences may be selected from sequences with at least 80%, 90% or 95% homology to SEQ ID NO: 1, SEQ ID NO: 2, SEQ ID NO: 3, and/or SEQ ID NO: 4

| Combinations | a1 | a2 | b2 | b1 |
|---|---|---|---|---|
| 1 | SEQ ID NO: 1 | SEQ ID NO: 3 | SEQ ID NO: 2 | SEQ ID NO: 4 |
| 2 | SEQ ID NO: 3 | SEQ ID NO: 1 | SEQ ID NO: 4 | SEQ ID NO: 2 |
| 3 | SEQ ID NO: 2 | SEQ ID NO: 4 | SEQ ID NO: 1 | SEQ ID NO: 3 |
| 4 | SEQ ID NO: 4 | SEQ ID NO: 2 | SEQ ID NO: 3 | SEQ ID NO: 1 |

In one embodiment according to the various aspects of the invention, the combination of sequence pairs is combination 1 as shown above. In one embodiment, the combination of sequence pairs is combination 2 as shown above. In one embodiment, the combination of sequence pairs is combination 3 as shown above. In one embodiment, the combination of sequence pairs is combination 4 as shown above.

In a preferred embodiment of the present invention, the polynucleotide comprises two sequence pairs (a1-a2) and (b2-b1) separated by a spacer sequence in which a1 is SEQ ID NO: 1, a2 is SEQ ID NO: 2, b2 is SEQ ID NO: 3, and b1 is SEQ ID NO: 4.

The sequences above are defined as follows (as disclosed in WO 2010/089437 incorporated herein by reference):

```
This is the sense sequence of omega gliadins.
                                      SEQ ID NO: 1
ccttcctcatctttgtcctccttgccatggcgatgaagatcgccactgc cgctagggagttaaaccctagcaacaaagagttacaatcacctcaacaa tcattttcccatcaacaacaaccatttccacagcagccatatccacaac aaccatatccatcacagcaaccatatccatcgcaacaaccattt This is the sense sequence of alpha, beta,
gamma gliadins.
                                      SEQ ID NO: 2
caacaacaactgattccatgcagggatgttgtattgcaacaacacagca tagcgtatggaagctcacaagttttgcaacaaagtacttaccagctggt gcaacaattgtgttgtcagcagctgtggcagatcccgagcagtcgcgg tgccaggccatccacaatgttat This is the antisense sequence of alpha, beta,
gamma gliadins.
                                      SEQ ID NO: 3
ataacattgtggatggcctggcaccgcgactgctcggggatctgccaca gctgctgacaacacaattgttgcaccagctggtaagtactttgttgcaa aacttgtgagcttccatacgctatgctgtgttgttgcaatacaacatcc ctgcatggaatcagttgttgttg This is the antisense sequence of omega gliadins
                                      SEQ ID NO: 4
aaatggttgttgcgatggatatggttgctgtgatggatatggttgttgt ggatatggctgctgtggaaatggttgttgttgatgggaaaatgattgtt gaggtgattgtaactctttgttgctagggtttaactccctagcggcagt ggcgatcttcatcgccatggcaaggaggacaaagatgaggaagg
```

The polynucleotide used in the various aspects of the invention confers, when expressed in a plant post-transcriptional silencing of all of the mRNAs (messenger RNA) that code for all types of wheat gliadins (ω, α, β, and γ gliadins) and increases lysine content in the plant. This is essentially due to the specific design of the sense and antisense subsequences whose generated siRNA hybridizes with all of the mRNA of the α, β, γ, and ω gliadins of wheat.

Thus, the invention also relates to plants with reduced gliadin/gluten content and increased lysine content.

The invention also relates to methods as described above which comprises silencing ω, α, β, and γ gliadins. For example, the invention also relates to a method for silencing ω, α, β, and γ gliadins and increasing lysine content in a plant, plant part or plant product derived therefrom comprising introducing and expressing a polynucleotide that is at least 80%, at least 90% or at least 95% identical to a sequence comprising two sequence pairs (a1-a2) and (b2-b1) separated by a spacer sequence in which:
  a. the sequences a1, a2, b1, and b2 are different sequences and are selected from SEQ ID NO: 1, SEQ ID NO: 2, SEQ ID NO: 3, or SEQ ID NO: 4, wherein
  b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
  c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4.

In another aspect, the invention relates to a use of a nucleic acid construct comprising a polynucleotide that is at least 80%, at least 90% or at least 95% identical to a sequence comprising two sequence pairs (a1-a2) and (b2-b1) separated by a spacer sequence in which:
  a. the sequences a1, a2, b1, and b2 are different sequences and are selected from SEQ ID NO: 1, SEQ ID NO: 2, SEQ ID NO: 3, or SEQ ID NO:4, wherein
  b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
  c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4
in silencing ω, α, β, and γ gliadins and increasing lysine content in a plant, plant part thereof or plant product.

Related methods for producing feed or food compositions are also within the scope of the invention. Thus, the invention relates to a method for increasing lysine content and silencing ω, α, β, and γ gliadins in a food or feed composition comprising
  a) introducing and expressing a nucleic acid construct comprising a polynucleotide that is at least 80%, at least 90% or at least 95% identical to a sequence comprising two sequence pairs (a1-a2) and (b2-b1) separated by a spacer sequence in which:
    a. the sequences a1, a2, b1, and b2 are different sequences and are selected from SEQ ID NO: 1, SEQ ID NO: 2, SEQ ID NO: 3, or SEQ ID NO: 4, wherein
    b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
    c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4 in a plant
  b) obtaining a progeny plant derived from the plant of step a) and
  c) preparing a food composition from said plant or part thereof.

In another aspect, the invention relates to a method for treating a patient suffering from a condition associated with lysine deficiency and from coeliac disease comprising providing in the diet of a person or administering or a person in need thereof an effective amount of a food composition or food supplement obtained by producing a plant or plant product with increased lysine content and reduced gluten content said method comprising a) introducing into said plant and expressing a polynucleotide that is at least 80%, at least 90% or at least 95% identical to a sequence comprising two sequence pairs (a1-a2) and (b2-b1) separated by a spacer sequence in which:
   a. the sequences a1, a2, b1, and b2 are different sequences and are selected from SEQ ID NO: 1, SEQ ID NO: 2, SEQ ID NO: 3, or SEQ ID NO: 4, wherein
   b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
   c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4
b) obtaining a progeny plant derived from said plant wherein ω, α, β, and γ gliadins are silenced and
c) and preparing a food composition or food supplement from said plant or plant part.

In preferred embodiments of the various aspects of the invention present invention, the polynucleotide comprises two sequence pairs (a1-a2) and (b2-b1) separated by a spacer sequence in which a1 is SEQ ID NO: 1, a2 is SEQ ID NO: 2, b2 is SEQ ID NO: 3, and b1 is SEQ ID NO: 4.

The spacer sequence may be any suitable sequence and can be designed using methods in the art. The spacer is at least 10 nucleotides long. According to one preferred embodiment, the polynucleotide comprises two sequence pairs (a1-a2) and (b2-b1) as described herein in which the spacer sequence is SEQ ID NO: 5. The sequence SEQ ID NO: 5 is a fragment of an intron of the gene Ubi1 that codes for maize ubiquitin. Other suitable spacer sequences are known to the skilled person. Preferably, the spacer sequence is a non-coding sequence that is eliminated after the process of forming dsRNA. The function of the spacer sequence is to act as a hinge for the sequence pairs described so that pairing or hybridization of the RNA sequences coding for the polynucleotide may take place.

Also included are the sequences that are complementary to any of the polynucleotides described herein.

The polynucleotide described herein may be comprised in a vector such as an expression vector. The term "vector" refers to a DNA fragment that has the capacity to replicate itself in a particular host, and, as the term indicates, may serve as a vehicle for multiplying another DNA fragment that has been fused to it (an insert). "Insert" refers to a DNA fragment that is fused to the vector; in the case of the present invention, the vector comprises the polynucleotide of the invention, which, when fused thereto, can replicate itself in the corresponding host. Vectors may be plasmids, cosmids, bacteriophages, or viral vectors, without excluding other types of vectors that meet the present definition of vector.

The term "plant" as used herein encompasses whole plants, ancestors and progeny of the plants and plant parts, including seeds, fruit, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

The various aspects of the invention described herein clearly extend to any plant cell or any plant produced, obtained or obtainable by any of the methods described herein, and to all plant parts and propagules thereof unless otherwise specified. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The various aspects of the invention also extend to harvestable parts of a plant of the invention as described above such as, but not limited to seeds, leaves, fruits, flowers, stems, roots, rhizomes, tubers and bulbs.

A part of a plant as used according to various aspects of the invention described herein preferably refers to seeds or grain, for example wheat grain.

According to the various aspects of the invention described herein, a plant product is derived from a harvestable part of such a plant, such as dry pellets or powders, flour, oil, fat and fatty acids, starch or proteins. In a preferred embodiment, the plant product is flour or semolina. The term "flour" as it is understood in the present invention refers to the product obtained by milling of any seed or plants of the genus *Triticum*, with the bran or husk of the seed removed to a greater or lesser degree. The term "semolina" refers to coarse flour (slightly milled wheat seeds), i.e., fragments of the endosperm with a variable amount of seed husks.

According to the various aspects of the invention, the plant may be a monocot or dicot plant. Preferably, the plant is a monocot crop plant.

According to preferred embodiments of the various aspects of the invention described herein, the plant is wheat and belongs to the genus *Triticum*.

In a preferred embodiment of the method of the invention, the invention therefore relates to a method for increasing lysine content in a plant of the genus *Triticum*, part thereof or a product derived therefrom comprising
a) introducing and expressing a polynucleotide that is at least 80%, at least 90% or at least 95% identical to a sequence comprising two sequence pairs (a1-a2) and (b2-b1) separated by a spacer sequence in which:
   a. the sequences a1, a2, b1, and b2 are different sequences and are selected from SEQ ID NO: 1, SEQ ID NO: 2, SEQ ID NO: 3, or SEQ ID NO: 4 wherein
   b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
   c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4
b) obtaining a progeny plant derived from said plant;
c) choosing a progeny plant with increased lysine content.

Step b can be carried out by measuring the lysine content in said plant progeny, plant part or plant product derived therefrom and comparing the lysine content to that of a control plant.

In another preferred embodiment, the invention relates to the use of a polynucleotide that is at least 80% identical to a sequence comprising two sequence pairs (a1-a2) and (b2-b1) separated by a spacer sequence in which:
   a. the sequences a1, a2, b1, and b2 are different sequences and are selected from SEQ ID NO: 1, SEQ ID NO: 2, SEQ ID NO: 3, or SEQ ID NO: 4, wherein
   b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
   c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4
in increasing lysine content in a plant of the genus *Triticum* a plant, plant product or food or feed composition.

The plant part is preferably wheat (grain) and the product is preferably flour or bread.

The plant is selected from the list that includes, but is not limited to, *Triticum aestivum, T. aethiopicum, T. araraticum, T. boeoticum, T. carthlicum, T. compactum, T. dicoccoides, T. dicoccum, T. durum, T. ispahanicum, T. karamyschevii, T. macha, T. militinae, T. monococcum, T. polonicum, T. repens, T. spelta, T. sphaerococcum, T. timopheevii, T. turanicum, T. turgidum, T. urartu, T. vavilovii* and *T. zhukovskyi*.

According to another embodiment the various aspects of the invention described herein, the plant is of the species *Triticum aestivum* or *Triticum turgidum*. According to another preferred embodiment, the plant belongs to the cultivar Bobwhite or the cultivar Don Pedro. More preferably, the cultivars BW208 and BW2003 (Bobwhite), which belong to the wheat species *Triticum aestivum* L. ssp *aestivum*, and the variety Don Pedro, which belongs to the wheat species *Triticum turgidum* L. ssp *durum*, are selected.

Bobwhite is the name of the cultivar obtained from the International Maize and Wheat Improvement Center (CIMMYT). BW208 and BW2003 are different Bobwhite lines. Don Pedro is a hard wheat variety, also from CIMMYT.

In one embodiment, the polynucleotide used in the various aspects of the invention comprises a regulatory element operably linked to its 5' end.

The term "regulatory element" is used interchangeably herein with "control sequence" and "promoter" and all terms are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences.

The term "regulatory element" also encompasses a synthetic fusion molecule or derivative that confers, activates or enhances expression of a nucleic acid molecule in a cell, tissue or organ.

A "plant promoter" comprises regulatory elements, which mediate the expression of a coding sequence segment in plant cells. Accordingly, a plant promoter need not be of plant origin, but may originate from viruses or microorganisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or comprise a suitable promoter which expresses the gene at the right point in time and with the required spatial expression pattern. For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes are known to the skilled person and include for example beta-glucuronidase or beta-galactosidase.

The term "operably linked" as used herein refers to a functional linkage between the promoter sequence and the gene of interest, such that the promoter sequence is able to initiate transcription of the gene of interest.

For example, the nucleic acid sequence may be expressed using a promoter that drives overexpression. Overexpression according to the invention means that the transgene is expressed at a level that is higher than expression of endogenous counterparts driven by their endogenous promoters. For example, overexpression may be carried out using a strong promoter, such as a constitutive promoter. A "constitutive promoter" refers to a promoter that is transcriptionally active during most, but not necessarily all, phases of growth and development and under most environmental conditions, in at least one cell, tissue or organ. Examples of constitutive promoters include the cauliflower mosaic virus promoter (CaMV35S or 19S), rice actin promoter, maize ubiquitin promoter, rubisco small subunit, maize or alfalfa H3 histone, OCS, SAD1 or 2, GOS2 or any promoter that gives enhanced expression. Alternatively, enhanced or increased expression can be achieved by using transcription or translation enhancers or activators and may incorporate enhancers into the gene to further increase expression. Furthermore, an inducible expression system may be used, where expression is driven by a promoter induced by environmental stress conditions (for example the pepper pathogen-induced membrane protein gene CaPIMP1 or promoters that comprise the dehydration-responsive element (DRE), the promoter of the sunflower HD-Zip protein gene Hahb4, which is inducible by water stress, high salt concentrations and ABA or a chemically inducible promoter (such as steroid- or ethanol-inducible promoter system). The promoter may also be tissue-specific. The types of promoters listed above are described in the art. Other suitable promoters and inducible systems are also known to the skilled person.

In another embodiment, a tissue-specific promoter, preferably a seed specific promoter, may be used. This is a promoter that is transcriptionally active predominantly in plant seeds, substantially to the exclusion of any other parts of a plant, whilst still allowing for any leaky expression in these other plant parts. Examples of seed specific promoters are those that regulate the expression of genes encoding seed storage proteins (e.g zein from maize (*Zea mays* L.), phaseolin from kidney bean (*Phaseolus vulgaris* L.) or napin from *Brassica*), seed coat proteins or acyl carrier protein are joined to other than the homologous gene and introduced into a plant cell host for integration into the genome to provide for seed-specific transcription. Such genes are known in the art.

According to a more preferred embodiment, the gene expression-regulating sequence is SEQ ID NO: 6 and/or SEQ ID NO: 7. The sequence SEQ ID NO: 6 corresponds to the sequence of a promoter of the γ gliadin gene that shows a duplication in a proline box. SEQ ID NO: 7 corresponds to the sequence of a promoter of the D-hordein gene (the second nucleotide of this gene has the accession number AY998009 and belongs to the species *Hordeum chilense*). Both promoters are expressed in the endosperm of the seeds.

In one embodiment, the promoter is a constitutive or strong promoter. In a preferred embodiment, the regulatory sequence is an inducible promoter, a stress inducible promoter or a tissue specific promoter. The stress inducible promoter is selected from the following non limiting list: the HaHB1 promoter, RD29A (which drives drought inducible expression of DREB1A), the maize rab17 drought-inducible promoter, P5CS1 (which drives drought inducible expression of the proline biosynthetic enzyme P5CS1), ABA- and drought-inducible promoters of Arabidopsis Glade A PP2Cs (ABI1, ABI2, HAB1, PP2CA, HAI1, HAI2 and HAI3) or their corresponding crop orthologs.

The nucleic acid sequence is introduced into said plant through a process called transformation. The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plants is now a routine technique in many species. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts, electroporation of protoplasts, microinjection into plant material, DNA or RNA-coated particle bombardment, infection with (non-integrative) viruses and the like. Transgenic plants, including transgenic crop plants, are preferably produced via *Agrobacterium tumefaciens* mediated transformation. According to the invention, the nucleic acid is preferably stably integrated in the transgenic plants genome and the progeny of said plant therefore also comprises the transgene.

To select transformed plants, the plant material obtained in the transformation is, in certain embodiments, subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. Alternatively, the transformed plants are screened for the presence of a selectable marker such as the ones described above.

Following DNA or nucleic acid transfer and regeneration, putatively transformed plants may also be evaluated, for instance using Southern analysis, for the presence of the gene of interest, copy number and/or genomic organisation. Alternatively or additionally, expression levels of the newly introduced nucleic acid may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

In another aspect, the invention relates to a method for producing a food or feed composition with increased lysine content comprising producing a transgenic plant with improved lysine content said method comprising a) introducing into said plant and expressing a polynucleotide that is at least 80%, at least 90% or at least 95% identical to a sequence comprising two sequence pairs (a1-a2) and (b2-b1) separated by a spacer sequence in which:
  a. the sequences a1, a2, b1, and b2 are different sequences and are selected from SEQ ID NO: 1, SEQ ID NO: 2, SEQ ID NO: 3, or SEQ ID NO: 4, wherein
  b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
  c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4 b) obtaining a progeny plant derived from the plant or plant cell of step a)

c) preparing a food or feed composition from said plant or plant part.

Preferably, the composition is a feed composition.

Embodiments of the polynucleotide are as described elsewhere herein. Preferred plants, in particular of the genus *Triticum* are as described elsewhere herein. Preferably, the food composition is flour or products using flour, such as bread.

In one embodiment, the method further comprises the step of selecting a lysine enriched part of said plant. Preferably, this is seeds, for example *Triticum* grain.

The method may further comprise screening plants for those that comprise the polynucleotide construct described herein and which have increased lysine content and selecting a plant that has an increased lysine content. In another embodiment, further steps include measuring the lysine content in said plant progeny, part thereof or product derived, for example the food composition, therefrom and comparing the lysine content to that of a control plant. Preferably, the progeny plant is stably transformed and comprises the exogenous polynucleotide which is heritable maintained in the plant cell and the method may include steps to verify that the construct is stably integrated. The method may also comprise the additional step of collecting seeds from the selected progeny plant.

In another aspect, the invention relates to a method for providing improved nutrition to a human or animal comprising feeding said human or animal on a diet comprising a food or feed composition obtained by a method for producing a transgenic plant with improved lysine content said method comprising a) introducing into said plant and expressing a polynucleotide that is at least 80%, at least 90% or at least 95% identical to a sequence comprising two sequence pairs (a1-a2) and (b2-b1) separated by a spacer sequence in which:
  a. the sequences a1, a2, b1, and b2 are different sequences and are selected from SEQ ID NO: 1, SEQ ID NO: 2, SEQ ID NO: 3, or SEQ ID NO: 4, wherein
  b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
  c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4 b) obtaining a progeny plant derived from the plant of step a) and c) preparing a food or feed composition from said plant or plant part.

Embodiments of the polynucleotide are as described elsewhere herein. Preferred plants, in particular of the genus *Triticum* are as described elsewhere herein. Preferably, the food composition is flour or products using flour, such as bread.

In one embodiment, the method further comprises the step of selecting a lysine enriched part of said plant. The method may further comprise screening plants for those that comprise the polynucleotide construct above and which have an increased lysine content and selecting a plant that has an increased lysine content. In another embodiment, further steps include measuring the lysine content in said plant progeny, part thereof or product derived therefrom and comparing the lysine content to that of a control plant. Preferably, the progeny plant is stably transformed and comprises the exogenous polynucleotide which is heritable as a fragment of DNA maintained in the plant cell and the method may include steps to verify that the construct is stably integrated. The method may also comprise the additional step of collecting seeds from the selected progeny plant.

In another aspect, the invention relates to a method for treating a condition associated with lysine deficiency comprising administering to a patient or animal in need thereof an effective amount of a food composition of food supplement obtained by producing a plant or plant product with increased lysine content said method comprising a) introducing into said plant and expressing a polynucleotide that is at least 80%, at least 90% or at least 95% identical to a sequence comprising two sequence pairs (a1-a2) and (b2-b1) separated by a spacer sequence in which:
  a. the sequences a1, a2, b1, and b2 are different sequences and are selected from SEQ ID NO: 1, SEQ ID NO: 2, SEQ ID NO: 3, or SEQ ID NO: 4, wherein
  b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
  c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4 b) obtaining a progeny plant derived from said plant and c) and preparing a food composition or food supplement from said plant or plant part.

The method can comprise the step of selecting patients with a condition that would benefit from said treatment. Conditions associated with lysine deficiency include appetite loss or deficiencies, such as delays, in growth and development, fatigue, mood changes, anxiety, cold sores and herpes simplex infections.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The invention is further described in the following non-limiting examples.

EXAMPLES

Example 1. Construction of the Vectors pGhp-ω/α/β/γ and pDhp-ω/α/β/γ and Containing Transgenic Wheat Plants The procedure as described in WO2010/089437 and Gil-Humanes et al (both incorporated herein by reference) was used.

1.1 Synthesis of α/β/γ and ω Gliadin Sequences.

The DNA sequences deposited in the Genebank belonging to wheat α/β/γ and ω gliadins were aligned separately, and the regions showing the greatest degree of homology were identified. Based on these alignments, we selected a 170 bp sequence of α/β/γ gliadins and another 191 bp sequence of ω gliadins and designed the primers Alpha_hp-F (SEQ ID NO: 8) and Alpha_hp-R (SEQ ID NO: 9) for amplification of the α/β/γ fragment and the primers Omega_III-F (SEQ ID NO: 10) and Omega_III-R (SEQ ID NO: 11) for amplification of the ω fragment (Table 1). The PCR conditions for the two fragments were as follows: cDNA of *T. aestivum* cv Bobwhite synthesized from 50 ng of total RNA extracted from immature grains, 1.5 mM of $MgCl_2$, 0.2 mM of dNTPs, 0.2 µM of each primer, 1× buffer, and 0.625 units of a mixture of polymerases in a 100:1 ratio of Tth (*Thermus thermophilus*) to Pfu (*Pyrococcus furiosus*) (BIOTOOLS, Madrid, Spain) in a final reaction of 25 µl. The conditions of the PCR cycles were as follows: an initial pass of 94° C. 5 min, 35 cycles of 94° C. 30 sec, 55° C. 30 sec, and 72° C. 30 sec; and a final extension of 72° C. 4 min in a GeneAmp PCR system 9700 thermocycler (Applied Biosystems). The products of each PCR were purified using the GFX PCR DNA Purification Kit (Amersham Biosciences, Amersham, UK) and were sequenced by the firm Secugen SL. In order to achieve overlapping of the α/β and ω fragments, the ω gliadin fragment was again amplified using an overlapping primer (overlapping Omega III R (SEQ ID NO: 12) together with the direct primer SEQ ID NO: 10), and the α/β gliadin fragment was again amplified using another overlapping primer, overlapping Alpha F (SEQ ID NO: 13), together with the reverse primer SEQ ID NO: 9) which added to each fragment 12 base pairs that were complementary with the other fragment. By means of the latter amplifications, we obtained two fragments that complemented each other between the 3' end of the ω gliadin fragment and the 5' end of the α/β/γ gliadin fragment. The PCR conditions were the same as described previously; the product of these reactions was separated in 1% agarose gel and the band corresponding to each fragment was purified with the QUIAquick Gel Extraction Kit (QUIAGEN Inc., Valencia, Calif.). The final overlapping PCR was carried out using 10 ng of the α/β/γ purified overlapping fragment, 10 ng of the purified ω fragment, 1.5 mM of $MgCl_2$, 0.2 mM of dNTPs, 0.2 µM of the primer alpha_hp-F, 0.2 µM of the primer omega_III-R, 1× buffer, and 0.625 units of a 100:1 mixture of Tth/Pfu polymerases in a final reaction of 50 µl. The conditions of the PCR cycles were as follows: an initial pass of 94° C. 2 min, 35 cycles of 94° C. 30 sec, 57° C. 30 sec, and 72° C. 30 sec; and a final extension of 72° C. 4 min in a GeneAmp PCR system 9700 thermocycler (Applied Biosystems). The product of these PCR was separated in 1% agarose gel and the band showing the size corresponding to the ω/α/β (361 bp) fragment was purified with the QUIAquick Gel Extraction Kit (QUIAGEN Inc., Valencia, Calif.) and cloned in the plasmid TOPO (Invitrogen, Carlsbad, Calif.). This plasmid comprises the sites attL1 and attL2 that allow transference through recombination of the gene of interest into any Gateway® vector that comprises the sites attR1 and attR2.

1.2 Obtaining the Transformation Vectors pGhp-ω/α/β/γ and pDhp-ω/α/β/γ.

The transformation vector was synthesized using the vector puc18 (2616 bp). The various fragments that comprise the transformation vector pGhp-ω/α/β/γ were introduced one by one into the multiple cloning site of the vector puc18. The fragment Nost (272 bp) was extracted from the vector pANDA-β by restriction with the enzyme EcoRI and introduced into the puc18, giving rise to puc18_Nost. Next, the fragment attRsense_GUS_attRantisense (4.4 kb) of the vector pANDA was extracted by restriction combined with the enzymes SacI and KpnI and introduced into the vector puc18_Nost, giving rise to puc18_attR_GUS_Nost. This fragment contained the sites attR1 and attR2 with sense and antisense sequences separated by a linking segment of 1 kb (gus linker). This gus linker sequence was substituted for the Ubi intron fragment (1019 bp) previously cloned in our laboratory by restriction with the enzyme EcoRV, producing the plasmid puc18_attR_Ubi_Nost. Finally the gliadin promoter (885 bp) was introduced by double restriction with the enzymes SphI and XhoI, producing the plasmid puc18_Gli_attR_Ubi_Nost.

The D-hordein gene promoter (836 bp) was also introduced by double restriction with the enzymes SphI and XhoI, producing the vector puc18_D_attR_Ubi_Nost. The difference between the vectors pGhp-ω/α/β/γ and pDhp-ω/α/β/γ is that the former contains the promoter of wheat γ gliadins and the latter contains the promoter of Barley D-hordein.

The next step was the introduction of the fragment ω/α/β into the plasmids puc18_Gli_attR_Ubi_Nost and puc18_D_attR_Ubi_Nost. The plasmid TOPO+ω/α/β contained the sites attL1 and attL2, while the plasmids puc18_Gli_attR_Ubi_NOSt and puc18_D_attR_Ubi_Nost contained the sites attR1 and attR2 with sense and antisense sequences separated by the intron Ubi. This made it possible to carry out an LR recombination reaction using the kit Gateway® LR Clonase TM Enzyme Mix (Invitrogen, Carlsbad, Calif.) and following the manufacturer's instructions. The result was the introduction of the fragment ω/α/β/γ having sense and antisense sequences separated by the intron Ubi into the structure of the plasmids puc18_Gli_attR_Ubi_NOSt and puc18_D_attR_Ubi_Nost. The resulting vectors were designated pGhp-ω/α/β/γ and pDhp-ω/α/β/γ (FIG. 2) and were introduced by transformation into competent *E. coli* cells (DH5α) for their subsequent multiplication.

Example 2. Obtaining Transgenic Wheat Lines

Genetic transformation was carried out by biolistics using a system for accelerating particles with pressurized helium (PDS1000/He™. BIORAD, Hercules, Calif.). We used two genotypes of bread wheat (*Triticum aestivum* L.) cultivar Bobwhite (BW208 and BW2003) and one of hard wheat (*Triticum turgidum* ssp *durum*) cultivar Don Pedro to isolate the scutella from immature embryos. Isolation was carried out in a sterile environment using immature wheat grains collected 12-16 days after anthesis, previously sterilized by immersion for 3 min in a 70% ethanol solution, 10 min in a 20% sodium hypochlorite solution, and rinsing twice with sterile distilled $H_2O$. For genetic transformation, we used gold particles 0.6 µm in diameter and mixed in 1.5 pmoles/mg gold of the vector pGhp-ω/α/β/γ or the vector pDhp-ω/α/β/γ and 0.5 pmoles/mg of the vector pAHC25 (Christensen et al., 1996. *Transgenic Research* 5, 213-218). The conditions of each shot were as follows: 91.4 kPa (27 inHg) vacuum pressure, 7.584 MPa (1100 PSI) shot pressure, 6 cm shot distance, and 60 µg of the mixture of gold and plasmids per shot.

Cotransformation with the plasmid pAHC25, which contains the bar selection gene (resistance to phosphinothricin) and the uidA gene (synthesis of β-glucuronidase), allowed selection of the tissues transformed in media with 2 mg/l of phosphinothricin (PPT) and subsequent identification of transgenic tissues by means of the β-glucuronidase assay (GUS) in accordance with the protocol described by Jefferson (1987, *Plant Mol Biol Rep* 5:387-405). The media, the in vitro cultivation process, and regeneration of the plants were in accordance with Barro et al (Barro et al., 1998. *Theoretical and Applied Genetics* 97, 684-695).

The plants regenerated in in vitro cultivation were placed in the soil, and they were then subjected to the GUS assay per se and as described in the previous paragraph. From the plants that yielded a positive result in the GUS assay, DNA was extracted using DNAzol reagent (Invitrogen, Carlsbad, Calif.) following the manufacturer's instructions, and PCR was carried out to confirm the presence of the plasmids pGhp-ω/α/β/γ, pDhp-ω/α/β/γ, and pAHC25 in the genome of the adult plant. PCR conditions were as follows: 100 ng of DNA extracted from young leaves, 1.5 mM $MgCl_2$, 0.2 mM dNTPs, 0.2 μM of each primer, 1× buffer, and 0.625 units of polymerase Tth (BIOTOOLS, Madrid, Spain). The primers used were prGliF (SEQ ID NO: 14) and overlapping Omega_III_R (SEQ ID NO: 12) for the plasmid pGhp-ω/α/β/γ, prHorDF (SEQ ID NO: 15) and overlapping Omega_III_R (SEQ ID NO: 12) for the plasmid pDhp-ω/α/β/γ and BAR_F (SEQ ID NO: 16) and BAR_R (SEQ ID NO: 17) for pAHC25 (Table 3). The conditions of the PCR cycles were as follows: an initial pass of 94° C. 5 min, 35 cycles of 94° C. 30 sec, 55° C. 30 sec, and 72° C. 2 sec; and a final extension of 72° C. 7 min in a GeneAmp PCR system 9700 thermocycler (Applied Biosystems). The product of each PCR was separated by electrophoresis in 1% agarose gel, and the positive lines were selected for subsequent analysis.

TABLE 3

Primers and sequences used.

| Primer | 5' to 3' sequence |
| --- | --- |
| Alpha_hp_F | (SEQ ID NO: 8) |
| Alpha_hp_R | (SEQ ID NO: 9) |
| Omega_III_F | (SEQ ID NO: 10) |
| Omega_III_R | (SEQ ID NO: 11) |
| Overlapping Omega_III_R | (SEQ ID NO: 12) |
| Overlapping Alpha_F_ | (SEQ ID NO: 13) |
| prGli_F | (SEQ ID NO: 14) |
| prHorDF | (SEQ ID NO: 15) |
| BAR_F | (SEQ ID NO: 16) |
| BAR_R | (SEQ ID NO: 17) |

Example 3. Analysis of Amino Acid and Gliadin Content in Transgenic Lines

Plant Material.

Four transgenic transgenic low gluten lines of *Triticum aestivum* cv. Bobwhite 208 ('BW208') and three transgenic low-toxic gluten lines of *T. aestivum* cv. Bobwhite 2003 ('BW2003'), and their respective wild-type lines were assayed using a randomized complete block design with two replicates. Each block consisted in 9 plots of 7 m2 (5 m×1.4 m) with 6 rows of plants separated 0.2 m, and a seeding density of 360 seeds per m2. All the transgenic low-toxic gluten lines were described or obtained as described in WO2010/089437 and contained the inverted repeat (IR) fragments ω/α (vectors pGhp-ω/α and pDhp-ω/α) designed to down regulate all the groups of gliadins by RNAi.

Grain Milling.

White flour was obtained from each of the two independent repetitions of the transgenic and wild-type lines. Grains were hydrated to 16.5% humidity by addition of distilled water in two steps (24 h and 20 h before milling) with continuous shaking. Hydrated seeds (1 Kg) of each line were milled separately in two steps in a CD1 Chopin (Chopin Technologies, Villeneuve-la-Garenne Cedex, France) standardized test mill. In the first step white flour and wholemeal flour were obtained. The wholemeal flour was reloaded in a second step of milling, and the resultant white flour was blended with the obtained previously, resulting in a total yield of about 60%. To avoid cross-contamination between samples, all the removable pieces of the Chopin mill as well as the internal cylinders were brushed and blown with pressure air. Flour was stored at room temperature (RT) for a week. Commercial rice flour supplied by Harinera Derivats del Blat de Moro, S. L. (Parets del Vallés, Spain) was used to elaborate the gluten-free control bread.

Bread Baking.

Dough was prepared on a flour weight basis: for 300 g flour, 180 ml water (225 ml water for the rice flour), 3.6 g baker's yeast (Saf-Instant, Lesaffre, France) and 4.8 g table salt were added. Ingredients were mixed in a Farinograph (Brabender GmbH & Co. KG, Germany) for 4 min, and rested for 10 min with a plastic film cover to avoid drying. Dough was divided manually (50 g) and dough pieces were rolled mechanically in a ball homogenizer (Brabender GmbH & Co. KG, Germany). Dough pieces were placed on aluminum trays and fermented during 45 min at 30° C. Next, dough pieces were baked in an electrical convection oven (Eurofours, Gommegnies, France). The baking process was performed at fixed oven temperature of 180° C. for 16 min with 2 initial steam injections of 10 sec each. After baking, bread loaves were rested for 30 min at RT to cool down.

Bread Characterization.

Bread weight and volume were determined in three loaves from each sample. Bread volume was determined by the rapeseed displacement method. Moisture content of the loaves was determined following the ICC Method No. 110/1 (40), with a pre-conditioning step of the bread samples. Three loaves from each sample and their central slides were scanned (HP Scanjet 4400C, Hewlett-Packard, USA), and height and width were determined to subsequently calculate the width/height ratio.

Descriptive Sensory Analysis.

A panel of 11 trained assessors was selected to evaluate the bread samples (n=20; 10 samples with two repetitions) corresponding to the and wild type wheat flours, and the rice flour. The range of experience of the test panelists of participating in descriptive analysis and scale rating of a wide range of bread products varied from 3 to 20 years. All the individuals composing the panel gave their informed consent. The panel evaluated appearance, aroma, flavor, and overall acceptance of each sample in a blind tasting. For evaluation, a set of six samples was presented in slices (1 cm thick) on plastic dishes coded and served in a randomized order. In addition, assessors were provided with mineral water in order to cleanse their palate between tastings. Each assessor received a list of sensorial attributes and their definitions to guide them during the sample evaluation.

Wholemeal flour was used for the characterization of amino acids profile of transgenic and wild-type lines. Flour samples were hydrolyzed using chloric acid 6N and phenol, and then derivatized and analyzed. For the derivatization we used the AccQ Fluor reagent Kit (Waters). First, 20 μl of the hydrolyzed sample were mixed with 60 μl of buffer solution (0.2 M borate buffer), and afterwards 20 μl of derivatization reagent (2 mg/ml AQC) were added according to the manufacturer's instructions. After 10 min at 50° C., the solution was directly injected into the HPLC system with detection MS/MS (Varian 320-MS). The amino acid separation was carried out using 2.5 mM ammonium acetate (pH=5.75) as solvent A, and a solution of 2.5 mM ammonium acetate (pH=6) and acetonitrile (30:70, ammonium acetate:acetonitrile) as solvent B. The Pursuit XRs Ultra 2.8 C18 100×2.0 mm column (Agilent) was used as stationary phase, and the flow was 200 μl $min^{-1}$. The detection was performed by MS with the ionization mode ESI (positive and negative). The amount of amino acid is expressed as percentage of the total sample weight. The results are shown in Table 4.

TABLE 4

Amino acid content (%) of fresh flour samples of wild types and transgenic lines.

| Amino Acid (%) | BW208 | D793 | D894 | E82 | E33 | BW2003 | D874 | E93 | E140 |
|---|---|---|---|---|---|---|---|---|---|
| Aspartic acid | 1.11 | 1.30 | 1.31 | 1.36 | 1.26 | 1.00 | 1.45 | 1.44 | 1.24 |
| Glutamic acid | 4.47 | 2.86 | 3.31 | 2.76 | 3.10 | 4.16 | 3.16 | 3.15 | 3.26 |
| Alanine | 0.86 | 0.68 | 0.78 | 0.72 | 0.82 | 0.76 | 0.80 | 0.84 | 0.76 |
| Arginine | 1.54 | 2.29 | 2.27 | 2.27 | 2.27 | 1.44 | 2.35 | 2.47 | 2.17 |
| Asparagine | <0.05 | <0.05 | <0.05 | <0.05 | <0.05 | <0.05 | <0.05 | <0.05 | <0.05 |
| Cysteine | 0.57 | 0.71 | 0.75 | 0.67 | 0.71 | 0.51 | 0.70 | 0.68 | 0.67 |
| Phenylalanine | 0.96 | 0.72 | 0.83 | 0.63 | 0.67 | 0.88 | 0.71 | 0.72 | 0.69 |
| Glycine | 1.16 | 1.22 | 1.39 | 1.07 | 1.33 | 1.18 | 1.31 | 1.54 | 1.28 |
| Glutamine | 0.65 | 0.81 | 0.64 | 0.62 | 0.63 | 0.60 | 0.64 | 0.64 | 0.59 |
| Histidine | 0.64 | 0.52 | 0.42 | 0.63 | 0.51 | 0.55 | 0.46 | 0.57 | 0.50 |
| Isoleucine | 0.63 | 0.52 | 0.57 | 0.48 | 0.49 | 0.57 | 0.57 | 0.50 | 0.53 |
| Leucine | 1.24 | 1.17 | 1.33 | 1.06 | 1.11 | 1.13 | 1.19 | 1.13 | 1.13 |
| Lysine | 0.70 | 0.87 | 0.94 | 0.98 | 0.89 | 0.57 | 0.95 | 0.83 | 0.82 |
| Methionine | <0.05 | <0.05 | <0.05 | <0.05 | <0.05 | <0.05 | <0.05 | <0.05 | <0.05 |
| Proline | 1.80 | 0.82 | 1.16 | 0.87 | 1.09 | 1.66 | 1.04 | 1.18 | 1.22 |
| Serine | 1.05 | 1.24 | 1.43 | 1.20 | 1.28 | 0.99 | 1.36 | 1.12 | 1.11 |
| Tyrosine | 0.82 | 0.99 | 1.00 | 0.78 | 0.85 | 0.82 | 1.03 | 0.98 | 0.87 |
| Threonine | 0.61 | 0.68 | 0.71 | 0.64 | 0.68 | 0.56 | 0.67 | 0.65 | 0.65 |
| Tryptophan | <0.05 | <0.05 | <0.05 | <0.05 | <0.05 | <0.05 | <0.05 | <0.05 | <0.05 |
| Valine | 0.98 | 1.01 | 1.07 | 0.90 | 0.89 | 0.90 | 1.03 | 0.96 | 0.88 |

TABLE 5

Gliadin composition, protein content and some agronomic traits in transgenic and wild type lines

| Parameter | Plasmid 0 (wt) | Plasmid 5 (pDhp_ω/α) | Plasmid 6 (pGhp_ω/α) |
|---|---|---|---|
| Omega gliadins (μg/mg flour) | 10.802 | 6.8839 * | 7.0085 * |
| Gamma gliadins (μg/mg flour) | 26.736 | 5.061 * | 2.2652 * |
| Alpha gliadins (μg/mg flour) | 27.493 | 12.966 * | 10.286 * |
| Total gliadins (μg/mg flour) | 65.031 | 24.911 * | 19.56 * |
| HMW glutenins (μg/mg flour) | 6.3133 | 17.185 * | 17.638 * |
| LMW glutenins (μg/mg flour) | 12.623 | 16.537 * | 13.657 |
| Total glutenins (μg/mg flour) | 18.937 | 33.722 * | 31.295 * |
| Gliadins/Glutenins | 3.4341 | 0.7387 * | 0.6250 * |
| Total prolamins (μg/mg flour) | 83.968 | 58.634 * | 50.855 * |
| Non gluten proteins (% DW) | 4.3433 | 7.3852 * | 7.8092 * |
| Protein content (% DW) | 13.391 | 13.691 | 13.283 |
| Starch content (% DW) | 66.011 | 62.811 | 63.594 |
| G12 (ppm) | 29494 | 4796.1 * | 2832.3 * |
| 1000 Kernel weight (g) | 36.267 | 32.644 | 32.589 |
| Test weight (g/l) | 829.17 | 812.5 | 807.64 |
| SDSS (ml) | 9.2744 | 9.5811 | 8.2289 |
| Anthesis (days) | 149 | 147.89 | 147.67 |

Significant differences were identified at the 5% (*) probability level by the two-sided Dunnett's multiple comparisons with control indicated as (0) in plasmid combination.

As shown in FIG. 4, alpha, omega and gamma gliadins are downregulated in the transgenic lines. Non-gluten proteins are upregulated, i.e. globulins and albumins, are upregulated. This fraction contains proteins very rich in lysine.

CONCLUSION

Flour from transgenic wheat (low gluten) and wild types were compared in terms of amino acid composition (Table 3), gliadin and protein content (Table 4). Interestingly, the content of lysine was significantly increased in the flour of all the transgenic lines compared to the wild type, with increments that ranged between 24-67% with respect to the wild types. Non-gluten proteins that are rich in lysine, are upregulated.

REFERENCES

Gad Galili and Rachel Amir, Plant Biotechnology Journal (2013) 11, pp. 211-222 WHO Technical Report 935, 2007

E. T. Mertz, O. E. Nelson, L. S. Bates, Mutant gene that changes protein composition increases lysine content of maize endosperm Science 145, 279 (1964, 1964).

H. O. Geevers, J. K. Lake, in Quality Protein Maize, E. T. Merts, Ed. (American Association of Cereal Chemist, St. Paul, 1992), pp. 49-78.

D. V. Glover, in Quality Protein Maize, E. T. Mertz, Ed. (American Association of Cereal Chemist, St. Paul, 1992), pp. 49-78.

A. Frizzi et al., Modifying lysine biosynthesis and catabolism in corn with a single bifunctional expression/silencing transgene cassette. Plant Biotechnology Journal 6, 13 (January 2008).

N. M. Houmard et al., High-lysine corn generated by endosperm-specific suppression of lysine catabolism using RNAi. Plant Biotechnology Journal 5, 605 (2007-September 2007).

X. R. Wu et al., Altered expression of plant lysyl tRNA synthetase promotes tRNA misacylation and translational recoding of lysine. Plant J 50, 627 (May, 2007).

J. Gil-Humanes, F. Pistón, S. Tollefsen, L. M. Sollid, F. Barro, Effective shutdown in the expression of celiac disease-related wheat gliadin T-cell epitopes by RNA interference. Proc Natl Acad Sci USA 107, 17023 (2010).

Sequences Listing
The following sequences are referred to above.
spacer sequence from Zea mays
SEQ ID NO: 5
CACCTCCGCttcaaggta cgccgctcgt cctccccccc
cccccctctc taccttctct agatcggcgt tccggtccat
ggttagggcc cggtagttct acttctgttc atgtttgtgt
tagatccgtg tttgtgttag atccgtgctg ctagcgttcg
tacacggatg cgacctgtac gtcagacacg ttctgattgc
taacttgcca gtgtttctct ttggggaatc ctgggatggc
tctagccgtt ccgcagacgg gatcgatttc atgattttt
ttgtttcgtt gcataggggt tggtttgccc ttttccttta
tttcaatata tgccgtgcac ttgtttgtcg ggtcatcttt
tcatgctttt ttttgtcttg gttgtgatga tgtggtctgg
ttgggcggtc gttctagatc ggagtagaat tctgtttcaa
actacctggt ggatttatta attttggatc tgtatgtgtg
tgccatacat attcatagtt acgaattgaa gatgatggat
ggaaatatcg atctaggata ggtatacatg ttgatgcggg
ttttactgat gcatatacag agatgctttt tgttcgcttg
gttgtgatga tgtggtgtgg ttgggcggtc gttcattcgt
tctagatcgg agtagaatac tgtttcaaac tacctggtgt
atttattaat tttggaactg tatgtgtgtg tcatacatct
tcatagttac gagtttaaga tggatggaaa tatcgatcta
ggataggtat acatgttgat gtgggttta ctgatgcata
tacatgatgg catatgcagc atctattcat atgctctaac
cttgagtacc tatctattat aataaacaag tatgttttat
aattattttg atcttgatat acttggatga tggcatatgc
agcagctata tgtggatttt tttagccctg ccttcatacg
ctatttattt gcttggtact gtttcttttg tcgatgctca
ccctgttgtt tggtgttact t
Triticum sp. promoter sequence
SEQ ID NO: 6
ttccagaaaa aactttgcta atgtatgaca gttatgtagt
gaatattttc aacctaagga acattttaa tttatttttt
ataaaattat aattcgactt ggcattcgaa tttggatttg
agtttggtt tgaaacggaa agaggattag taaaatgatt
atgatgacat agcatcatta ggcatgagat tactgtagca
tgacatgggg gtgttacact tgtacaatat tcctaccctt
gacataaaag gagaatttga tgagtcatgt attgataacg
tatacaacat tactaccctt gacataaaag gagaatttga
tgagtcatgc attgataaca tgtacaagat tactatcagc
ttgttcatct taccatcata ttatacaaca ctacaagtta
gttttagaaa gaacaagagt ccacaacaaa tatcagaata
cttgcctgat ctatcttaac aacatgcaca aggacacaaa tttagtcccc cgcaagctat gaagatttgg tttatgtcta
acaacttgta cagatccaaa aggaatgcaa tccagataat
tgtttgacat gtaaagtgaa taagatgagt caatgccaat
tatcaagtat tcctcactct tagatgatat gtacaataaa
aagacaactt tgatgatcac tctgaaatta cgtttgtatg
tagtgccacc aaacacaaca taccaaataa ttagtttgat
aagcatcaaa tcacttttaa aaagaaagc aataatgaaa
agaaacctaa ccatggtagc yataaaaagg cctacaatat
gtagactcca taccatcatc catcgttcac acaactagag
cacaagcaga aaatcaaagt acgtagtagt taacgcaaat
ccacc Hordeum chilense promoter sequence
SEQ ID NO: 7
ccattaattg aactcattcg ggaagcggga aaatttccaa
ttctggtata aatcaaacta tttgacgcga attttctctg
aagatcatat gttaatttta gacatcactg accaaaggtt
tcagttggtt gagttttgtc acggatacaa gatgcttcca
tacgtcaaaa aattctacca acttttggta cggtgcctcg
tagcacggat agatcttgtg tgtcactgga tagatgttgt
gtgtcactag attgatattg tgagtcatag catggatttg
tgttgcctgg aaagggaatt acatgacaag caacaaaacc
tgaaatgagc ttttggaaag atgatttatc agtttacttg
ttccatgcaa gctaccttcc actactcgac atgcttagaa
gcttcgagtg cccgcggatt tgccaaagca atggctaaca
gacacatatt ctgccaaaaa cccagaacga taatcgcttc
tcgtagatga agagaacaga ccaagataca aacgtccaca
cttctgcaaa cagtacccca gaactaggat taagccgatt
acgtggcttt agcagaccgt ccaaaaaaac tgctttgcaa
agctccaatt cctccttgct tatccaattt cttttgtgtt
ggcaaactgc acttttttcca accgattctg ttcttcccgt
gtttcttctt aggctagcta acatagccgt gcacacagcc
atggtccgga accttcacct cgtccctata aaagcccagc
caatctccac aatctcttca tcaccgagaa caccgrgcac
cacgaaacta gagatcaatt cattgacagt cggatg

The invention claimed is:

1. A method for increasing lysine content in a plant, plant part or plant product derived therefrom comprising introducing and expressing a polynucleotide that is at least 80%, at least 90%, at least 95% identical to a sequence comprising two sequence pairs (a1-a2) and (b2-b1) separated by a spacer sequence in which:
   a) the sequences a1, a2, b1, and b2 are different sequences and are selected from SEQ ID NO: 1, SEQ ID NO: 2, SEQ ID NO: 3, or SEQ ID NO: 4, wherein
   b) if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
   c) if a1 is SEQ ID NO: 2 or SEQ ID NO: 3, b1 is SEQ ID NO: 3 or SEQ ID NO: 2, and a2 is SEQ ID NO: 1 or SEQ ID NO: 4, wherein said plant has increased lysine content compared to a control plant without said polynucleotide, wherein said lysine content is increased by about 20% to about 70%.

2. The method according to claim 1 said method further comprising the following steps:
   a) obtaining a progeny plant derived from said plant;
   b) measuring the lysine content in said plant progeny, plant part or plant product derived therefrom and
   c) comparing the lysine content to that of a control plant.

3. The method according to claim 1 wherein said plant part is a seed.

4. The method according to claim 1 wherein said plant product is a food composition.

5. The method according to claim 4 wherein said food composition is selected from flour or bread.

6. The method according to claim 1 wherein said plant product is a feed composition.

7. The method according to claim 1 wherein a1 is SEQ ID NO: 1, a2 is SEQ ID NO: 2, b2 is SEQ ID NO: 3, and b1 is SEQ ID NO: 4.

8. The method according to claim 1 wherein the spacer sequence is SEQ ID NO: 5.

9. The method according to claim 1 wherein said polynucleotide comprises a regulatory sequence operably linked to its 5' end.

10. The method according to claim 9 wherein the regulatory sequence is SEQ ID NO: 6 or SEQ ID NO: 7.

11. The method according to claim 1 wherein said plant belongs to the genus *Triticum*.

12. The method according to claim 11 wherein said plant *Triticum aestivum* or *Triticum turgidum*.

13. The method according to a claim 12 wherein said plant is a Bobwhite cultivar or a Don Pedro cultivar.

14. A method for increasing lysine content in a food or feed composition comprising
   a) introducing and expressing a nucleic acid construct comprising a polynucleotide that is at least 80%, at least 90%, at least 95% identical to a sequence comprising two sequence pairs (a1-a2) and (b2-b1) separated by a spacer sequence in which:
      a) the sequences a1, a2, b1, and b2 are different sequences and are selected from SEQ ID NO: 1, SEQ ID NO: 2, SEQ ID NO: 3, or SEQ ID NO: 4, wherein
      b) if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
      c) if a1 is SEQ ID NO: 2 or SEQ ID NO: 3, b1 is SEQ ID NO: 3 or SEQ ID NO: 2, and a2 is SEQ ID NO: 1 or SEQ ID NO: 4 in a plant,
   wherein said plant has increased lysine content compared to a control plant without said polynucleotide, wherein said lysine content is increased by about 20% to about 70%;
   b) obtaining a progeny plant derived from the plant of step a; and
   c) preparing a food composition from said plant or part thereof.

15. The method according to claim 14 said method further comprising the following steps:
   a) obtaining a progeny plant derived from said plant;
   b) measuring the lysine content in said plant progeny, plant part or plant product derived therefrom and
   c) comparing the lysine content to that of a control plant.

16. The method according to claim 14 wherein said food composition is flour or bread.

17. A method for providing improved nutrition to a human or animal comprising feeding said human or animal on a diet comprising a food or feed composition obtained by the producing a plant or plant product with increased lysine content said method comprising
   a) introducing into said plant and expressing a polynucleotide that is at least 80%, at least 90%, at least 95% identical to a sequence comprising two sequence pairs (a1-a2) and (b2-b1) separated by a spacer sequence in which:
      a) the sequences a1, a2, b1, and b2 are different sequences and are selected from SEQ ID NO: 1, SEQ ID NO: 2, SEQ ID NO: 3, or SEQ ID NO: 4, wherein
      b) if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
      c) if a1 is SEQ ID NO: 2 or SEQ ID NO: 3, b1 is SEQ ID NO: 3 or SEQ ID NO: 2, and a2 is SEQ ID NO: 1 or SEQ ID NO: 4,
   wherein said plant has increased lysine content compared to a control plant without said polynucleotide, wherein said lysine content is increased by about 20% to about 70%;
   b) obtaining a progeny plant derived from said plant; and
   c) preparing a food or feed composition from said plant or plant part.

18. A method for treating a condition associated with lysine deficiency comprising administering to a patient in need thereof an effective amount of a food composition of food supplement obtained by producing a plant or plant product with increased lysine content said method comprising
   a) introducing into said plant and expressing a polynucleotide that is at least 80%, at least 90% or at least 95% identical to a sequence comprising two sequence pairs (a1-a2) and (b2-b1) separated by a spacer sequence in which:
      a) the sequences a1, a2, b1, and b2 are different sequences and are selected from SEQ ID NO: 1, SEQ ID NO: 2, SEQ ID NO: 3, or SEQ ID NO: 4, wherein
      b) if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
      c) if a1 is SEQ ID NO: 2 or SEQ ID NO: 3, b1 is SEQ ID NO: 3 or SEQ ID NO: 2, and a2 is SEQ ID NO: 1 or SEQ ID NO: 4,
   wherein said plant has increased lysine content compared to a control plant without said polynucleotide, wherein said lysine content is increased by about 20% to about 70%;
   b) obtaining a progeny plant derived from said plant; and
   c) preparing a food composition or food supplement from said plant or plant part.

19. A method for increasing lysine content and silencing $\omega$, $\alpha$, $\beta$, and $\gamma$ gliadins in a plant, plant part or plant product derived therefrom comprising introducing and expressing a polynucleotide that is at least 80%, at least 90%, at least 95% identical to a sequence comprising two sequence pairs (a1-a2) and (b2-b1) separated by a spacer sequence in which:
   a) the sequences a1, a2, b1, and b2 are different sequences and are selected from SEQ ID NO: 1, SEQ ID NO: 2, SEQ ID NO: 3, or SEQ ID NO: 4, wherein
   b) if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
   c) if a1 is SEQ ID NO: 2 or SEQ ID NO: 3, b1 is SEQ ID NO: 3 or SEQ ID NO: 2, and a2 is SEQ ID NO: 1 or SEQ ID NO: 4,
wherein said plant has increased lysine content compared to a control plant without said polynucleotide, wherein said lysine content is increased by about 20% to about 70%.

* * * * *

SEQUENCE LISTING

<160> NUMBER OF SEQ ID NOS: 17

<210> SEQ ID NO 1
<211> LENGTH: 191
<212> TYPE: DNA
<213> ORGANISM: Artificial
<220> FEATURE:
<223> OTHER INFORMATION: Sense sequence of omega gliadins

<400> SEQUENCE: 1
ccttcctcat ctttgtcctc cttgccatgg cgatgaagat cgccactgcc gctagggagt     60
taaaccctag caacaaagag ttacaatcac ctcaacaatc attttcccat caacaacaac    120
catttccaca gcagccatat ccacaacaac catatccatc acagcaacca tatccatcgc    180
aacaaccatt t                                                         191

<210> SEQ ID NO 2
<211> LENGTH: 170
<212> TYPE: DNA
<213> ORGANISM: Artificial
<220> FEATURE:
<223> OTHER INFORMATION: Sense sequence of alpha, beta, gamma gliadins

<400> SEQUENCE: 2
caacaacaac tgattccatg cagggatgtt gtattgcaac aacacagcat agcgtatgga     60
agctcacaag ttttgcaaca agtacttac cagctggtgc aacaattgtg ttgtcagcag     120
ctgtggcaga tccccgagca gtcgcggtgc caggccatcc acaatgttat                170

<210> SEQ ID NO 3
<211> LENGTH: 170
<212> TYPE: DNA
<213> ORGANISM: Artificial
<220> FEATURE:
<223> OTHER INFORMATION: Antisense sequence of alpha, beta, gamma
      gliadins

<400> SEQUENCE: 3
ataacattgt ggatggcctg gcaccgcgac tgctcgggga tctgccacag ctgctgacaa     60
cacaattgtt gcaccagctg gtaagtactt tgttgcaaaa cttgtgagct tccatacgct    120
atgctgtgtt gttgcaatac aacatccctg catggaatca gttgttgttg                170

<210> SEQ ID NO 4
<211> LENGTH: 191
<212> TYPE: DNA
<213> ORGANISM: Artificial
<220> FEATURE:
<223> OTHER INFORMATION: Antisense sequence of omega gliadins

<400> SEQUENCE: 4
aaatggttgt tgcgatggat atggttgctg tgatggatat ggttgttgtg gatatggctg     60
ctgtggaaat ggttgttgtt gatgggaaaa tgattgttga ggtgattgta actctttgtt    120
gctagggttt aactccctag cggcagtggc gatcttcatc gccatggcaa ggaggacaaa    180
gatgaggaag g                                                         191

<210> SEQ ID NO 5
<211> LENGTH: 1011
<212> TYPE: DNA
<213> ORGANISM: Zea mays

<400> SEQUENCE: 5

| | |
|---|---|
| gttcaaggta cgccgctcgt cctccccccc cccccctctc taccttctct agatcggcgt | 60 |
| tccggtccat ggttagggcc cggtagttct acttctgttc atgtttgtgt tagatccgtg | 120 |
| tttgtgttag atccgtgctg ctagcgttcg tacacggatg cgacctgtac gtcagacacg | 180 |
| ttctgattgc taacttgcca gtgtttctct ttggggaatc ctgggatggc tctagccgtt | 240 |
| ccgcagacgg gatcgatttc atgattttt ttgtttcgtt gcatagggtt tggtttgccc | 300 |
| ttttcctta tttcaatata tgccgtgcac ttgtttgtcg ggtcatcttt tcatgctttt | 360 |
| ttttgtcttg gttgtgatga tgtggtctgg ttgggcggtc gttctagatc ggagtagaat | 420 |
| tctgtttcaa actacctggt ggatttatta attttggatc tgtatgtgtg tgccatacat | 480 |
| attcatagtt acgaattgaa gatgatggat ggaaatatcg atctaggata ggtatacatg | 540 |
| ttgatgcggg ttttactgat gcatatacag agatgctttt tgttcgcttg gttgtgatga | 600 |
| tgtggtgtgg ttgggcggtc gttcattcgt tctagatcgg agtagaatac tgtttcaaac | 660 |
| tacctggtgt atttattaat tttggaactg tatgtgtgtg tcatacatct tcatagttac | 720 |
| gagtttaaga tggatggaaa tatcgatcta ggataggtat acatgttgat gtgggtttta | 780 |
| ctgatgcata tacatgatgg catatgcagc atctattcat atgctctaac cttgagtacc | 840 |
| tatctattat aataaacaag tatgttttat aattattttg atcttgatat acttggatga | 900 |
| tggcatatgc agcagctata tgtggatttt tttagccctg ccttcatacg ctatttatt | 960 |
| gcttggtact gttctttttg tcgatgctca ccctgttgtt tggtgttact t | 1011 |

<210> SEQ ID NO 6
<211> LENGTH: 885
<212> TYPE: DNA
<213> ORGANISM: Triticum sp.

<400> SEQUENCE: 6

| | |
|---|---|
| ttccagaaaa aactttgcta atgtatgaca gttatgtagt gaatattttc aacctaagga | 60 |
| acatttttaa tttattttt ataaaattat aattcgactt ggcattcgaa tttggatttg | 120 |
| agttttggtt tgaaacggaa agaggattag taaaatgatt atgatgacat agcatcatta | 180 |
| ggcatgagat tactgtagca tgacatgggg gtgttacact tgtacaatat tcctacccctt | 240 |
| gacataaaag gagaatttga tgagtcatgt attgataacg tatacaacat tactacccctt | 300 |
| gacataaaag gagaatttga tgagtcatgc attgataaca tgtacaagat tactatcagc | 360 |
| ttgttcatct taccatcata ttatacaaca ctacaagtta gttttagaaa gaacaagagt | 420 |
| ccacaacaaa tatcagaata cttgcctgat ctatcttaac aacatgcaca aggacacaaa | 480 |
| tttagtcccc cgcaagctat gaagatttgg tttatgtcta acaacttgta cagatccaaa | 540 |
| aggaatgcaa tccagataat tgtttgacat gtaaagtgaa taagatgagt caatgccaat | 600 |
| tatcaagtat tcctcactct tagatgatat gtacaataaa aagacaactt tgatgatcac | 660 |
| tctgaaatta cgtttgtatg tagtgccacc aaacacaaca taccaaataa ttagtttgat | 720 |
| aagcatcaaa tcactttaa aaaagaaagc aataatgaaa agaaacctaa ccatggtagc | 780 |
| yataaaaagg cctacaatat gtagactcca taccatcatc catcgttcac acaactagag | 840 |
| cacaagcaga aaatcaaagt acgtagtagt taacgcaaat ccacc | 885 |

<210> SEQ ID NO 7
<211> LENGTH: 836
<212> TYPE: DNA
<213> ORGANISM: Hordeum chilense

<400> SEQUENCE: 7

```
ccattaattg aactcattcg ggaagcggga aaatttccaa ttctggtata aatcaaacta       60
tttgacgcga attttctctg aagatcatat gttaatttta gacatcactg accaaaggtt      120
tcagttggtt gagttttgtc acggatacaa gatgcttcca tacgtcaaaa aattctacca      180
acttttggta cggtgcctcg tagcacggat agatcttgtg tgtcactgga tagatgttgt      240
gtgtcactag attgatattg tgagtcatag catggatttg tgttgcctgg aaagggaatt      300
acatgacaag caacaaaacc tgaaatgagc ttttggaaag atgatttatc agttacttg       360 ttccatgcaa gctaccttcc actactcgac atgcttagaa gcttcgagtg cccgcggatt      420
tgccaaagca atggctaaca gacacatatt ctgccaaaaa cccagaacga taatcgcttc      480
tcgtagatga agagaacaga ccaagataca aacgtccaca cttctgcaaa cagtacccca      540
gaactaggat taagccgatt acgtggcttt agcagaccgt ccaaaaaaac tgctttgcaa      600
agctccaatt cctccttgct tatccaattt cttttgtgtt ggcaaactgc acttttttcca     660 accgattctg ttcttcccgt gtttcttctt aggctagcta acatagccgt gcacacagcc      720
atggtccgga accttcacct cgtccctata aaagcccagc caatctccac aatctcttca      780
tcaccgagaa caccgrgcac cacgaaaacta gagatcaatt cattgacagt cggatg        836
```

<210> SEQ ID NO 8
<211> LENGTH: 21
<212> TYPE: DNA
<213> ORGANISM: Triticum sp.

<400> SEQUENCE: 8

```
caacaacaac tgattccatg c                                                21
```

<210> SEQ ID NO 9
<211> LENGTH: 20
<212> TYPE: DNA
<213> ORGANISM: Triticum sp.

<400> SEQUENCE: 9

```
ayracattrt ggatggcytg                                                  20
```

<210> SEQ ID NO 10
<211> LENGTH: 21
<212> TYPE: DNA
<213> ORGANISM: Triticum sp.

<400> SEQUENCE: 10

```
ccttcctcat ctttgtcctc c                                                21
```

<210> SEQ ID NO 11
<211> LENGTH: 21
<212> TYPE: DNA
<213> ORGANISM: Triticum sp.

<400> SEQUENCE: 11

```
aaatggttgt tgcgatggat a                                                21
```

<210> SEQ ID NO 12
<211> LENGTH: 30
<212> TYPE: DNA
<213> ORGANISM: Triticum sp.

<400> SEQUENCE: 12

```
cagttgttgt tgaaatggtt gttgcgatgg                                       30
```

```
<210> SEQ ID NO 13
<211> LENGTH: 30
<212> TYPE: DNA
<213> ORGANISM: Triticum sp.

<400> SEQUENCE: 13
caacaaccat ttcaacaaca actgattcca                                        30

<210> SEQ ID NO 14
<211> LENGTH: 23
<212> TYPE: DNA
<213> ORGANISM: Triticum sp.

<400> SEQUENCE: 14
ttccagaaaa aactttgcta atg                                               23

<210> SEQ ID NO 15
<211> LENGTH: 20
<212> TYPE: DNA
<213> ORGANISM: Hordeum chilense

<400> SEQUENCE: 15
ccattaattg aactcattcg                                                   20

<210> SEQ ID NO 16
<211> LENGTH: 19
<212> TYPE: DNA
<213> ORGANISM: Streptomyces hygroscopicus

<400> SEQUENCE: 16
gtctgcacca tcgtcaacc                                                    19

<210> SEQ ID NO 17
<211> LENGTH: 20
<212> TYPE: DNA
<213> ORGANISM: Streptomyces hygroscopicus

<400> SEQUENCE: 17
gaagtccagc tgccagaaac                                                   20
```